US012195792B2

(12) United States Patent
Mauch et al.

(10) Patent No.: US 12,195,792 B2
(45) Date of Patent: Jan. 14, 2025

(54) DRIED AMPLIFICATION COMPOSITIONS

(71) Applicant: GEN-PROBE INCORPORATED, San Diego, CA (US)

(72) Inventors: Steven Mauch, San Diego, CA (US); Robert Stephen Dickson, San Diego, CA (US); Matthias Jost, San Diego, CA (US); Mark Filipowsky, San Marcos, CA (US); Donald Martin, Escondido, CA (US); Vladislav Nodelman, San Diego, CA (US); Cheryl Lynn Crowell, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 16/074,593

(22) PCT Filed: Feb. 3, 2017

(86) PCT No.: PCT/US2017/016592
§ 371 (c)(1),
(2) Date: Aug. 1, 2018

(87) PCT Pub. No.: WO2017/136782
PCT Pub. Date: Aug. 10, 2017

(65) Prior Publication Data
US 2019/0284604 A1 Sep. 19, 2019

Related U.S. Application Data

(60) Provisional application No. 62/291,770, filed on Feb. 5, 2016.

(51) Int. Cl.
*C12Q 1/686* (2018.01)
*C12Q 1/6804* (2018.01)

(52) U.S. Cl.
CPC ........... *C12Q 1/686* (2013.01); *C12Q 1/6804* (2013.01)

(58) Field of Classification Search
CPC .............................. C12Q 1/686; C12Q 1/6849
See application file for complete search history.

(56) References Cited

U.S. PATENT DOCUMENTS

| | | |
|---|---|---|
| 5,102,788 A | 4/1992 | Cole |
| 5,556,771 A | 9/1996 | Shen et al. |
| 5,593,824 A | 1/1997 | Treml et al. |
| 5,861,251 A | 1/1999 | Park et al. |
| 5,876,992 A | 3/1999 | De Rosier et al. |
| 6,153,412 A | 11/2000 | Park et al. |
| RE37,872 E | 10/2002 | Franks et al. |
| 6,684,524 B1 | 2/2004 | Sennhenn et al. |
| 6,908,759 B2 | 6/2005 | Jang |
| 6,910,720 B2 * | 6/2005 | Shimei .................. A61J 1/2089 |
| | | 285/331 |
| 7,964,350 B1 * | 6/2011 | Fekete .................. C12Q 1/6844 |
| | | 435/6.12 |
| 8,187,557 B2 | 5/2012 | Van Atta et al. |
| 8,426,134 B2 | 4/2013 | Piepenburg et al. |
| 8,470,261 B2 | 6/2013 | Eshoo et al. |
| 8,900,525 B2 | 12/2014 | Ponaka et al. |
| 2004/0235138 A1 * | 11/2004 | Weisburg ............. C12Q 1/6893 |
| | | 435/252.3 |
| 2005/0069898 A1 | 3/2005 | Moon et al. |
| 2006/0068398 A1 | 3/2006 | McMillan |
| 2007/0259348 A1 * | 11/2007 | Phadke .................. F26B 5/065 |
| | | 435/6.12 |
| 2012/0135394 A1 * | 5/2012 | Kim ..................... C12Q 1/6844 |
| | | 435/5 |
| 2014/0011184 A1 * | 1/2014 | DeCastro ............... G01N 25/04 |
| | | 435/3 |
| 2014/0295419 A1 * | 10/2014 | Zhang .................. C12Q 1/6865 |
| | | 435/6.11 |
| 2016/0032269 A1 * | 2/2016 | Gong ..................... C12P 19/34 |
| | | 435/91.2 |

FOREIGN PATENT DOCUMENTS

| | | | | |
|---|---|---|---|---|
| EP | 726310 B1 * | 7/2003 | ........... | C12N 9/1241 |
| EP | 1374827 A2 | 1/2004 | | |
| JP | 10-503383 A | 3/1998 | | |
| JP | 2007-252270 A | 10/2007 | | |
| WO | 2006/003439 A2 | 1/2006 | | |
| WO | 2006/119280 A2 | 11/2006 | | |
| WO | 2007/005626 A1 | 1/2007 | | |
| WO | 2008/090340 A2 | 7/2008 | | |
| WO | WO 2008/155524 A1 | 12/2008 | | |
| WO | WO-2010001162 A1 * | 1/2010 | ............. | C07H 21/00 |
| WO | 2010/141940 A1 | 12/2010 | | |

(Continued)

OTHER PUBLICATIONS

PCT International Search Report, International Application No. PCT/US2017/016592, Apr. 3, 2017.
PCT Written Opinion, International Application No. PCT/US2017/016592, Apr. 3, 2017.
UKIPO Combined Search and Examination Report under Sections 17 and 18(3), U.K. Application No. GB1701910.0, Dec. 5, 2017.
BD Sprint Advantage 96 Plate, Versatile PCR enzyme mix in a high-throughput format, BD Biosciences Clontech, 2002.
BD Sprint Advantage PCR Products User Manual, BD Biosciences Clontech, 2003, pp. 1-22.

(Continued)

*Primary Examiner* — Carolyn L Greene
(74) *Attorney, Agent, or Firm* — Alston & Bird LLP; Jeffrey E. Landes

(57) ABSTRACT

The disclosure provides dried compositions providing reagents for nucleic acid amplification, which are essentially free of inorganic salts. Lack of inorganic salts increases stability of such compositions and decreases formation of byproducts. Salts required for use of enzymes in the composition are supplied on reconstitution.

17 Claims, 8 Drawing Sheets

(56) References Cited

FOREIGN PATENT DOCUMENTS

| WO | 2010/144682 A1 | 12/2010 | | |
|---|---|---|---|---|
| WO | WO 2013/101783 A2 | 7/2013 | | |
| WO | 2014/114956 A1 | 7/2014 | | |
| WO | WO-2016034892 A1 * | 3/2016 | ..... | C12Q 2565/1015 |
| WO | 2017/136782 A1 | 8/2017 | | |

OTHER PUBLICATIONS

GE Healthcare, "Illustra puReTaq Ready-To-Go PCR Beads", (Product Booklet) 2006, pp. 1-22.

Richards et al., "Thermal stability landscape for Klenow DNA Ploymerase as a function of pH and salt concentration," Biochimica et aBiophysica Acta 1764, 2006, pp. 1546-1552.

Li et al., "The protective effects of trehalose o freeze-drying and LAMP reagents storage," Progress In Fishery Sciences, vol. 33, No. 5, p. 95-101, (Oct. 2012), English Abstract.

Fu et al., "Pharmaceutical Excipients," China Press of Traditional Chinese Medicine, pp. 110-113, (Oct. 2008), see IDS transmittal for brief statement of relevance.

EP 23203507.1 Extended European Search Report mailed Feb. 22, 2024.

Lorenz, "Polymerase Chain Reaction: Basic Protocol Plus Troubleshooting and Optimization Strategies," J. Vis. Exp., (63), e3998, doi:10.279/3998, (2012).

KR 10-2018-7022388 Notice of Preliminary Rejection dated Jan. 20, 2024, English translation.

\* cited by examiner

R&D Bulk Hold Pellets: Day 22 at 45°C - Flu-A at TCID50=10°

| Sample | Liquid Ctrl | 45 min | 4 hr | 8 hr |
|---|---|---|---|---|
| Avg Ct | 34.3 | 34.5 | 34.4 | 33.9 |
| SD Ct | 0.39 | 0.58 | 0.32 | 0.60 |

Average Total Flourescence values: 824,895; 806,570; 855,772; 1,162,967

20140328DM: R&D Bulk Hold Time

FIG. 2

DRIED AMPLIFICATION COMPOSITIONS

CROSS REFERENCE TO RELATED APPLICATIONS

This application is a national stage entry of PCT/US2017/016592 filed Feb. 3, 2017, which claims the benefit of U.S. Provisional Patent Application No. 62/291,770, filed Feb. 5, 2016, which is hereby incorporated by reference.

BACKGROUND

Commercial kits for performing nucleic acid amplification and/or detection reactions often contain reagents such as enzymes, including one or more of a polymerase such as a DNA dependent DNA polymerase or an RNA dependent DNA polymerase (e.g., reverse transcriptase), nucleotides, detergents, buffers, primers, probes and inorganic salt, including $MnCl_2$, $MgCl_2$, NaCl, and KCl (Innis et al, (1990) *PCR Protocols: A Guide to Methods and Applications, Ch. 1, Optimizations of PCRs*). Inorganic salts are useful in stabilizing certain components of a nucleic acid reaction mixture and in performing certain steps of a nucleic acid based reaction. However these same salts are undesirable components of formulations that are to be lyophilized and/or stored before use, as these salts have a negative impact on the stability and driness of a lyophilized composition.

Magnesium ions have been reported to increase activity of polymerases and other enzymes. Potassium chloride has been reported to facilitate nucleic acid hybridizations. A number of inorganic salts, including those with magnesium, have also been reported to protect proteins under various conditions of stress including heat, chaotropic agent exposure and lyophilization (see e.g., Liu et al (2007) *FEBS Letters.* 581:1047; Kanaya et al (1996) *J. Biol. Chem.* 271:32729; Innis et al, (1990) *PCR Protocols: A Guide to Methods and Applications, Ch. 1, Optimizations of PCRs*; Menendez et al (1998) *J. Biol. Chem.* 273:167; Janeway et al (1993) *Biochemistry.* 32:1601; Fox et al (1971) *J. Biol. Chem.* 246:5739; Chang et al (2002) *J. Biol. Chem.* 277: 277:4663; Rutter et al (1958) *J. Biol. Chem.* 233:374; Huszar et al (1981) *J. Virol.* 37:580-588; Wang (2000) *Int. J. Pharmaceutics.* 203:1-60).

The presence of the salts in a reaction mixture is believed necessary to avoid denaturation of enzymes. However, stability of a lyophilized substance is affected by the hygroscopicity of any salts present in the lyopholized cake. Hygroscopicity of a lyophilized substance in turn affects the time available to package the lyophilized substance, and affects the duration and conditions under which the lyophilized substance can be stored and shipped. The undesired rehydration of a lyophilized substance negatively impacts the activity of lyophilized components. To minimize the negative impact from undesired rehydration of a lyophilized substance, long term storage of such substances is usually performed with refrigeration.

SUMMARY

Disclosed herein are compositions comprising an aqueous solution containing a polymerase and/or a reverse transcriptase, a bulking agent, a detergent and an organic buffer, wherein the aqueous solution has an inorganic salt concentration of 7 mM or less.

In some embodiments of the aqueous solutions, the aqueous solution further comprises at least one oligonucleotide useful for performing a molecular assay. In some embodiments, the aqueous solution comprises oligonucleotides for performing a multiplex molecular assay. In some embodiments, the at least one oligonucleotide includes an amplification oligomer. In some embodiments, the at least one oligonucleotide includes a detection probe. In some embodiments, the detection probe includes a label covalently joined to an oligonucleotide. In some embodiments, the label is a fluorescent or chemiluminescent molecule. In some embodiments, the detection probe is a taqman detection probe. In some embodiments, the detection probe oligonucleotide is configured to form a hairpin. In some embodiments, the at least one oligonucleotide includes an adaptor oligonucleotide. In some embodiments, the at least one oligonucleotide includes an adaptor configured to form a hairpin. In some embodiments, the at least one oligonucleotide includes a target capture probe. In some embodiments, the target capture probe has a target hybridizing portion that specifically hybridizes to a target nucleic acid under stringent conditions. In some embodiments, the molecular assay includes a nucleic acid amplification assay. In some embodiments, the molecular assay includes a nucleic acid detection assay. In some embodiments, the molecular assay includes a nucleic acid sequencing assay. In some embodiments, the molecular assay includes a nucleic acid hybridization assay.

In some embodiments of the aqueous solutions, the bulking agent is trehalose, raffinose, or a combination thereof. In some embodiments, the bulking agent is present at a concentration from about 0.16 M to about 0.32 M.

In some embodiments of the aqueous solutions, the inorganic salts are present at a mass per microliter from about 0.029 µg/µl to about 0.373 µg/µl. In some embodiments, the aqueous solution contains from about 0.029 µg/µl of sodium chloride to about 0.292 µg/µl of sodium chloride. In some embodiments, the aqueous solution contains from about 0.019 µg/µl of potassium chloride to about 0.373 µg/µl of potassium chloride. In some embodiments, the aqueous solution contains from about 0.006 µg/µl of sodium ion to about 0.115 µg/µl of sodium ion. In some embodiments, the aqueous solution contains from about 0.010 µg/µl of potassium ion to about 0.196 µg/µl of potassium ion. In some embodiments, the aqueous solution contains from about 0.009 µg/µl chloride ion to about 0.355 µg/µl chloride ion.

In some embodiments of the aqueous solutions, the aqueous solution comprises an inorganic salt concentration of 4 mM or less. In some embodiments, the aqueous solution comprises a mass per microliter of inorganic salt from about 0.234 µg to about 0.298 µg. In some embodiments, the aqueous solution comprises a mass per microliter of chloride ions from about 0.071 µg to about 0.284 µg. In some embodiments, the aqueous solution comprises an inorganic salt concentration of 3 mM or less. In some embodiments, the aqueous solution comprises a mass per microliter of inorganic salt from about 0.175 µg to about 0.224 µg. In some embodiments, the aqueous solution comprises a mass per microliter of chloride ions from about 0.053 µg to about 0.213 µg. In some embodiments, the aqueous solution comprises an inorganic salt concentration of 2 mM or less. In some embodiments, the aqueous solution comprises a mass per microliter of inorganic salt from about 0.117 µg to about 0.149 µg. In some embodiments, the aqueous solution comprises a mass per microliter of chloride ions from about 0.036 µg to about 0.142 µg. In some embodiments, the aqueous solution comprises an inorganic salt concentration of 1 mM or less. In some embodiments, the aqueous solution comprises a mass per microliter of inorganic salt from about 0.058 µg to about 0.075 µg. In some embodiments, the aqueous solution comprises a mass per microliter of chloride ions from about 0.018 µg to about 0.071 µg. In some embodiments, the aqueous solution comprises an inorganic salt concentration of 500 uM or less. In some embodiments, the aqueous solution comprises a mass per microliter of inorganic salt from about 0.029 µg to about 0.037 µg. In some embodiments, the aqueous solution comprises a mass per microliter of chloride ions from about 0.009 µg to about 0.036 µg.

In some embodiments of the aqueous solutions, the inorganic salt concentration of the aqueous solution is less than 1 mM sodium chloride. In some embodiments, the aqueous solution does not contain sodium chloride. In some embodiments, the aqueous solution contains less than 1 mM magnesium ions. In some embodiments, the aqueous solution contains less than 0.1 mM magnesium ions, suitably no magnesium ions.

In some embodiments of the aqueous solutions, the aqueous solution further comprises deoxynucleotide triphosphates (dNTPs). In some embodiments, the dNTPs include dATP at a concentration of from 0.1 mM to 0.3 mM in the aqueous solution. In some embodiments, the dATP is at a concentration of 0.2 mM in the aqueous solution. In some embodiments, the dNTPs include dGTP at a concentration of from 0.1 mM to 0.3 mM in the aqueous solution. In some embodiments, the dGTP is at a concentration of 0.2 mM in the aqueous solution. In some embodiments, the dNTPs include dCTP at a concentration of from 0.1 mM to 0.3 mM in the aqueous solution. In some embodiments, the dCTP is at a concentration of 0.2 mM in the aqueous solution. In some embodiments, the dNTPs include dTTP at a concentration of from 0.2 mM to 0.6 mM in the aqueous solution. In some embodiments, the dNTPs include dUTP at a concentration of from 0.2 mM to 0.6 mM in the aqueous solution. In some embodiments, the dNTPs include labeled dNTPs.

In some embodiments of the aqueous solutions, the polymerase is at a concentration from about 0.20 U/µl to about 0.72 U/µl in the aqueous solution. In some embodiments, the polymerase is in the aqueous solution at a concentration selected from: 0.25 U/µl, 0.30 U/µl to, 0.32 U/µl, 0.4 U/µl, 0.5 U/µl, 0.45 U/µl, and 0.72 U/µl. In some embodiments, the polymerase is a hot-start polymerase. In some embodiments, the polymerase is a recombinant Taq DNA polymerase bound by an antibody that specifically blocks polymerase activity of the polymerase. In some embodiments, the polymerase is a chemically modified recombinant Taq DNA polymerase, wherein the chemical modification inhibits polymerase activity of the polymerase. In some embodiments, the polymerase is modified for incorporation of labeled dNTPs into a nucleic acid extension reaction product.

In some embodiments of the aqueous solutions, the aqueous solution comprises a reverse transcriptase at a concentration from about 0.1 U/µl to about 0.6 U/µl. In some embodiments, the reverse transcriptase is an AMV reverse transcriptase. In some embodiments, the reverse transcriptase is an MMLV reverse transcriptase.

In some embodiments of the aqueous solutions, the aqueous solution further comprises an RNase inhibitor. In some embodiments, the RNase inhibitor is present in the aqueous solution at a concentration from about 0.12 U/µl to about 0.20 U/µl.

In some embodiments of the aqueous solutions, the aqueous solution further comprises a chelating agent. In some embodiments, the chelating agent is selected from the group consisting of Ethylenediaminetetraacetic acid (EDTA), Ethylenediamine-N,N'-disuccinic acid (EDDS), Methylglycinediacetic acid (MGDA), Diethylene triamine pentaacetic acid (DTPA), and Ethylene glycol-bis(β-aminoethyl ether)-N,N,N',N'-tetraacetic acid (EGTA). In some embodiments, the chelating agent is EDTA and is present in the aqueous solution at a concentration from 1.5 mM to 2.0 mM.

Disclosed herein are dried forms of the above described aqueous solutions.

Disclosed herein are dried compositions comprising an enzyme selected from the group consisting of a polymerase and a reverse transcriptase, a bulking agent, an organic buffer, and a detergent. The dried compositions also comprise one or more inorganic salts, wherein the one or more inorganic salts are present in the dried composition at a mass that is 0.350% or less of the total mass of the dried composition.

In some embodiments of the dried compositions, the one or more inorganic salts are present in the dried composition at a mass that is from about 0.311% to about 0.024% of the total mass of the dried composition. In some embodiments, the one or more inorganic salts are selected from the group consisting of: sodium chloride, potassium chloride and both sodium chloride and potassium chloride.

In some embodiments of the dried compositions, the dried composition further comprises at least one oligonucleotide useful for performing a molecular assay. In some embodiments, the dried composition comprises oligonucleotides for performing a multiplex molecular assay. In some embodiments, the at least one oligonucleotide includes an amplification oligomer. In some embodiments, the at least one oligonucleotide includes a detection probe. In some embodiments, the detection probe includes a label covalently joined to an oligonucleotide. In some embodiments, the label is a fluorescent or chemiluminescent molecule. In some embodiments, the detection probe is a taqman detection probe. In some embodiments, the detection probe oligonucleotide is configured to form a hairpin. In some embodiments, the at least one oligonucleotide includes an adaptor oligonucleotide. In some embodiments, the at least one oligonucleotide includes an adaptor configured to form a hairpin. In some embodiments, the at least one oligonucleotide includes a target capture probe. In some embodiments, the target capture probe has a target hybridizing portion that specifically hybridizes to a target nucleic acid under stringent conditions. In some embodiments, the molecular assay includes a nucleic acid amplification assay. In some embodiments, the molecular assay includes a nucleic acid detection assay. In some embodiments, the molecular assay includes a nucleic acid sequencing assay. In some embodiments, the molecular assay includes a nucleic acid hybridization assay.

In some embodiments of the dried compositions, the bulking agent is trehalose, raffinose, or a combination thereof.

In some embodiments of the dried compositions, the dried composition further comprises deoxynucleotide triphosphates (dNTPs).

In some embodiments of the dried compositions, the polymerase is a hot-start enzyme. In some embodiments, the polymerase is a recombinant Taq DNA polymerase bound to an antibody that specifically blocks polymerase activity. In some embodiments, the polymerase is a chemically modified recombinant Taq DNA polymerase. In some embodiments, the polymerase is modified for incorporation of labeled dNTPs into a nucleic acid extension reaction product.

In some embodiments of the dried compositions, the reverse transcriptase is an AMV reverse transcriptase, or the reverse transcriptase is an MMLV reverse transcriptase.

In some embodiments of the dried compositions, the dried composition further comprises an RNase inhibitor.

In some embodiments of the dried compositions, the dried composition further comprises a chelating agent. In some embodiments, the chelating agent is selected from the group consisting of EDTA, EGTA, EDDS, DTPA, and MGDA.

Disclosed herein are methods of forming a mixture for use in performing a nucleic acid based amplification reaction, the method comprising combining a reconstitution solution and a dried composition as described above, wherein the reconstitution solution comprises at least one inorganic salt.

In some embodiments of the methods, the reconstitution solution comprises an inorganic salt concentration of less than 1 mM. In some embodiments, the reconstitution solution comprises an inorganic salt selected from the group consisting of sodium ions, potassium ions, magnesium ions, manganese ions, chloride ions, and combinations thereof. In some embodiments, the reconstitution solution comprises $MgCl_2$ at a concentration from about 3.8 mM to about 4.4 mM, or comprises KCl at a concentration from about 50 mM to about 80 mM, or both. In some embodiments, the reconstitution solution comprises a $MgCl_2$ concentration that is in excess of the $MgCl_2$ concentration needed in the reconstituted dried composition (the amount of $MgCl_2$ needed in the reconstituted dried composition is determined based on a number of factors such as enzyme requirements, molecular assay requirements, and molecular assay optimization results). These reconstitution solutions comprising excess $McCl_2$ are referred to as universal reconstitution solutions. Universal reconstitution solutions are useful for reconstituting dried compositions containing a variety of components for performing different molecular assays. By way of example only, a universal reconstitution solution can comprise $MgCl_2$ at concentration X. A dried composition #1 has a requirement for $MgCl_2$ at a concentration of 0.8×, while a dried composition #2 has a requirement for $MgCl_2$ at a concentration of 0.95×. Both the dried composition #1 and the dried composition #2 are reconstituted with the same universal reconstitution solution and the $MgCl_2$ concentrations in the reconstituted dried compositions are reduced to the desired levels by use of a chelating agent. Preferably, dried compositions #1 and #2 are each formulated (e.g., in the pre-dried bulk reagent) to include a chelating agent in an amount that will sequester the excess $MgCl_2$ from the subsequently used universal reconstitution solution. Upon reconstitution the chelating agent will sequester some of the $MgCl_2$, thereby leaving free in solution only the desired concentration of $MgCl_2$ (e.g., 0.8× and 0.95× respectively for this exemplary description).

In some embodiments of the methods, the reconstitution solution comprises, methyl paraben at a mass concentration from about 0.012% w/v to about 0.020% w/v, or comprises propyl paraben at a mass concentration from about 0.006% w/v to about 0.010% w/v, or comprises absolute ethanol at a volume concentration from about 0.20% v/v to about 0.30% v/v, or a combination thereof. In some embodiments, the concentration of the methyl paraben in the reconstitution solution is 0.016% w/v. In some embodiments, the concentration of propyl paraben in the reconstitution solution is 0.008% w/v. In some embodiments, the absolute ethanol is present in the reconstitution solution at about 0.26% v/v.

Disclosed herein are methods for preparing a dried composition for use in performing a molecular assay, such as a nucleic acid based amplification reaction, a nucleic acid based detection reaction, a nucleic acid based sequencing reaction, a nucleic acid based hybridization reaction, and combinations thereof. In some embodiments, the methods comprise a drying step selected from the group of methods consisting of: dehydration, desiccation, lyophilization, and spray-drying. In some embodiments, the methods comprise the drying steps of: (i) freezing an aqueous solution composition as described herein, thereby forming a frozen form of the composition; and (ii) exposing the frozen form of the composition to lyophilization conditions, thereby forming a dried form of the composition. In some embodiments, the aqueous composition is dried in a lyophilizer to produce a lyophilized composition.

Dried compositions are useful for nucleic acid based reactions (e.g., amplification and/or detection reactions) following reconstitution. Dried compositions that have been subjected to prolonged exposure to humid environments surprisingly provide robust amplification and/or detection results when reconstituted and used in nucleic acid amplification and/or detection assays. The dried form of the compositions that have been exposed to a humid environment, wherein the absolute humidity level of the humid environment is greater than 2.3 grams of water per cubic meter of air for a period of time of up to 3 hours; preferably for a period of time from 90 minutes to 180 minutes; preferably about 90 minutes; or preferably about 180 minutes, are then reconstituted and are useful in nucleic acid amplification and/or detection assays. In certain embodiments, the reconstituted form of dried compositions are useful in amplification and/or detection reactions even though the dried compositions were subjected to exposure to a humid environment, wherein the relative humidity level of the humid environment is 10% or less for a period of time of up to 8 hours. In certain embodiments, the reconstituted form of the dried compositions are useful in amplification and/or detection reactions even though the dried compositions were subjected to exposure to a humid environment, wherein the absolute humidity level of the humid environment is 2.3 grams of water per cubic meter of air at 25° C. or less for a period of time of up to 8 hours. In certain embodiments an aqueous bulk reagent is incubated for a prolonged period of time, then all or a portion of the aqueous bulk reagent is dried to form a dried compositions, which, upon reconstitution of the dried compositions, surprisingly provide robust nucleic acid amplification and/or detection results when used in a nucleic acid amplification and/or detection assay.

In some embodiments, the dried composition is stored in a sealed vessel. In some embodiments, the dried composition is exposed to a humid environment before the step of storing the dried composition in the sealed vessel, wherein the absolute humidity level of the humid environment is greater than 2.3 grams of water per cubic meter of air. In some embodiments, the pre-dried aqueous solution is stored at room temperature for up to 8 hours before the drying step is initiated. In some embodiments, the pre-dried aqueous solution is stored at room temperature for a time period of time from about 45 minutes to about 8 hours before the drying step was initiated. In some embodiments, the dried composition is exposed to a humid environment before the step of storing the dried composition in the sealed vessel, wherein the relative humidity level of the humid environment is less than 10%. In some embodiments, the dried composition is exposed to a humid environment before the step of storing the dried composition in the sealed vessel, wherein the absolute humidity level of the humid environment is 2.3 grams of water per cubic meter of air at 25° C. or less. In some embodiments, the dried aqueous solution is stored at room temperature for up to 8 hours before the step of storing the dried composition in the sealed vessel.

Disclosed herein are kits for use in performing a molecular assay. In some embodiments, the kits are for performing a nucleic acid based amplification reaction. In some embodiments, the kits are for performing a nucleic acid based detection reaction. In some embodiments, the kits are for performing a nucleic acid based sequencing reaction. In some embodiments, the kits are for performing a nucleic acid based hybridization reaction. In some embodiments, the kits are for performing a combination of molecular assays such as, for example, a nucleic acid based amplification and detection reaction. In some embodiments, the kits comprise within a vessel a dried composition as described herein. In some embodiments, the kits comprise in a vessel a solution for reconstituting a dried composition for use in a molecular assay such as, for example, an amplification reaction and/or a detection reaction. In some embodiments, the kits comprise a first vessel containing a dried composition as described herein, and a second vessel containing a reconstitution solution comprising $MgCl_2$ at a concentration from about 3.8 mM to about 4.4 mM. In some embodiments, the first vessel is a multiwell plate comprising one or more wells. In some embodiments, at least one of the one or more wells contains a dried composition. In some embodiments, each of the one or more wells contain a dried composition. In some embodiments, two or more of the one or more wells contain a dried composition for performing different molecular assays. In one aspect of this embodiment, each dried pellet in the two or more wells has a different $MgCl_2$ concentration requirement. Further in an aspect of this embodiment, each dried pellet having a different $MgCl_2$ concentration requirement is reconstituted with a universal reconstitution having a $MgCl_2$ concentration equal to or in excess of the additional $MgCl_2$ required for each molecular assay. In some embodiments, at least one of the one or more wells contains a dried single unit dose pellet that contains a percent mass of inorganic salt to mass of pellet of 0.311% or less. In some embodiments, each of the one or more wells contains a dried single unit dose pellet that contains a percent mass of inorganic salt to mass of pellet of 0.311% or less. In some embodiments, the first vessel is constructed from a material with a low moisture-vapor transmission rate, that is thermally conductive, that is optically transparent, that provides low autofluorescence, or a combination thereof. In one embodiment, the first vessel comprises a cap to seal the opening of the vessel. In some embodiments, the cap is a foil, a plug, or an elastomeric substance. In some embodiments, the cap has a low moisture-vapor transmission rate. In some embodiments, the first and second vessels are incorporated within a device adapted for automated transfer of the reconstitution solution from the second vessel into the first vessel.

BRIEF DESCRIPTIONS OF THE FIGURES

FIG. 2 shows influence of room temperature storage time (storage of the bulk reagent prior to lyophilization) on activity recovered from lyophilized pellet. Bulk reagent was stored under a number of conditions, dried, and used in a nucleic acid amplification and detection reaction to identify influenza A from a sample.

Figure 3:
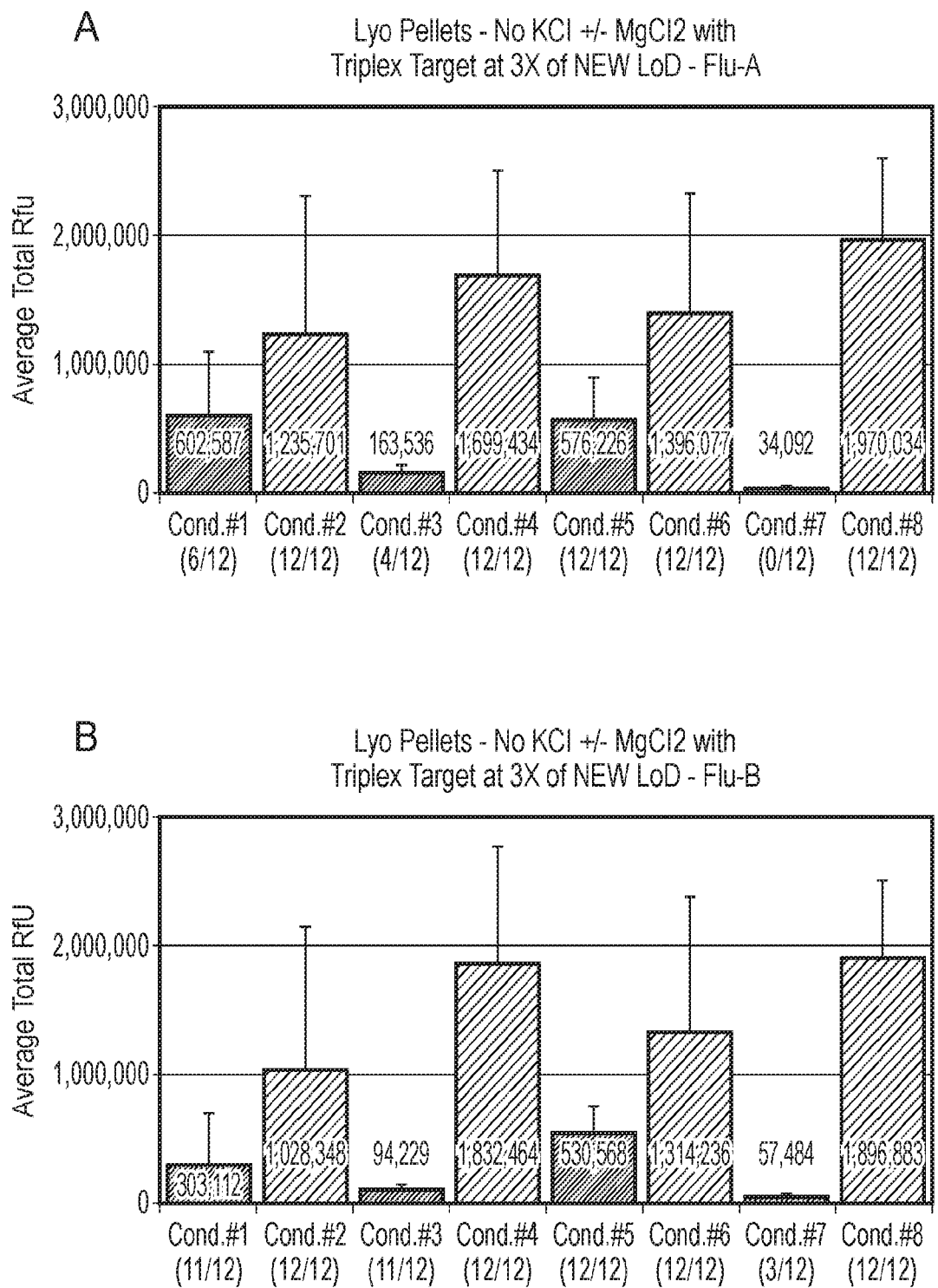
Figure 3:
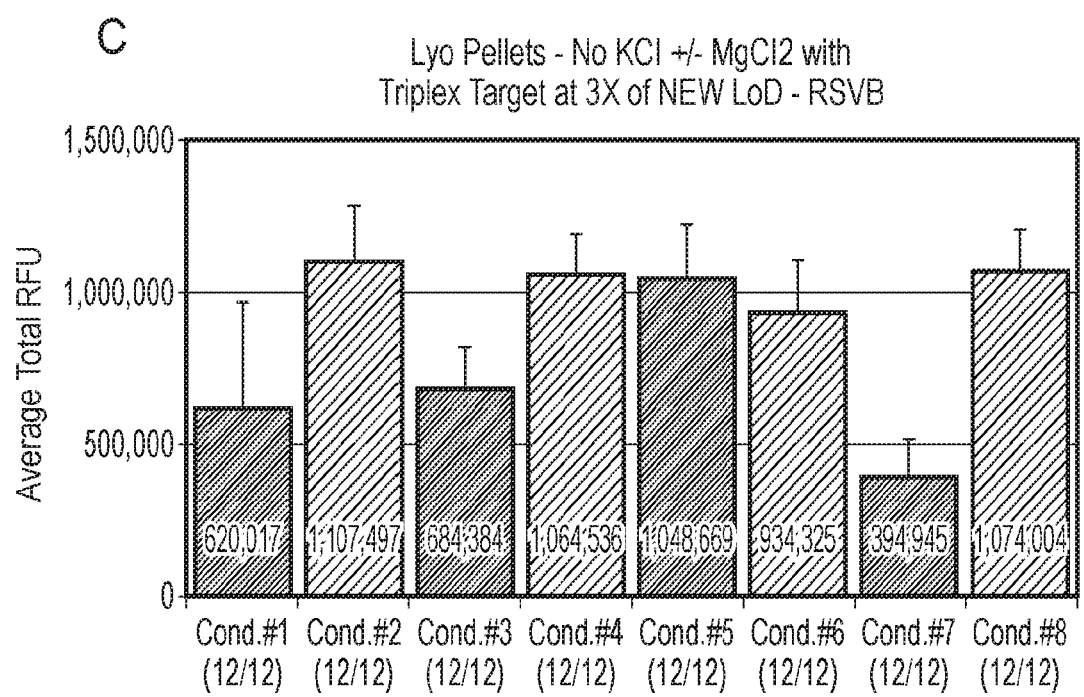

FIGS. 3A, 3B, and 3C are histograms plots illustrating the relative fluorescent units (RFU) data for amplification and detection assays performed using reconstituted forms of dried single unit dose (SUD) pellet compositions made from bulk reagents without KCl, with or without $MgCl_2$ and incubated at room temperature or on ice for a time period.

Figure 4:
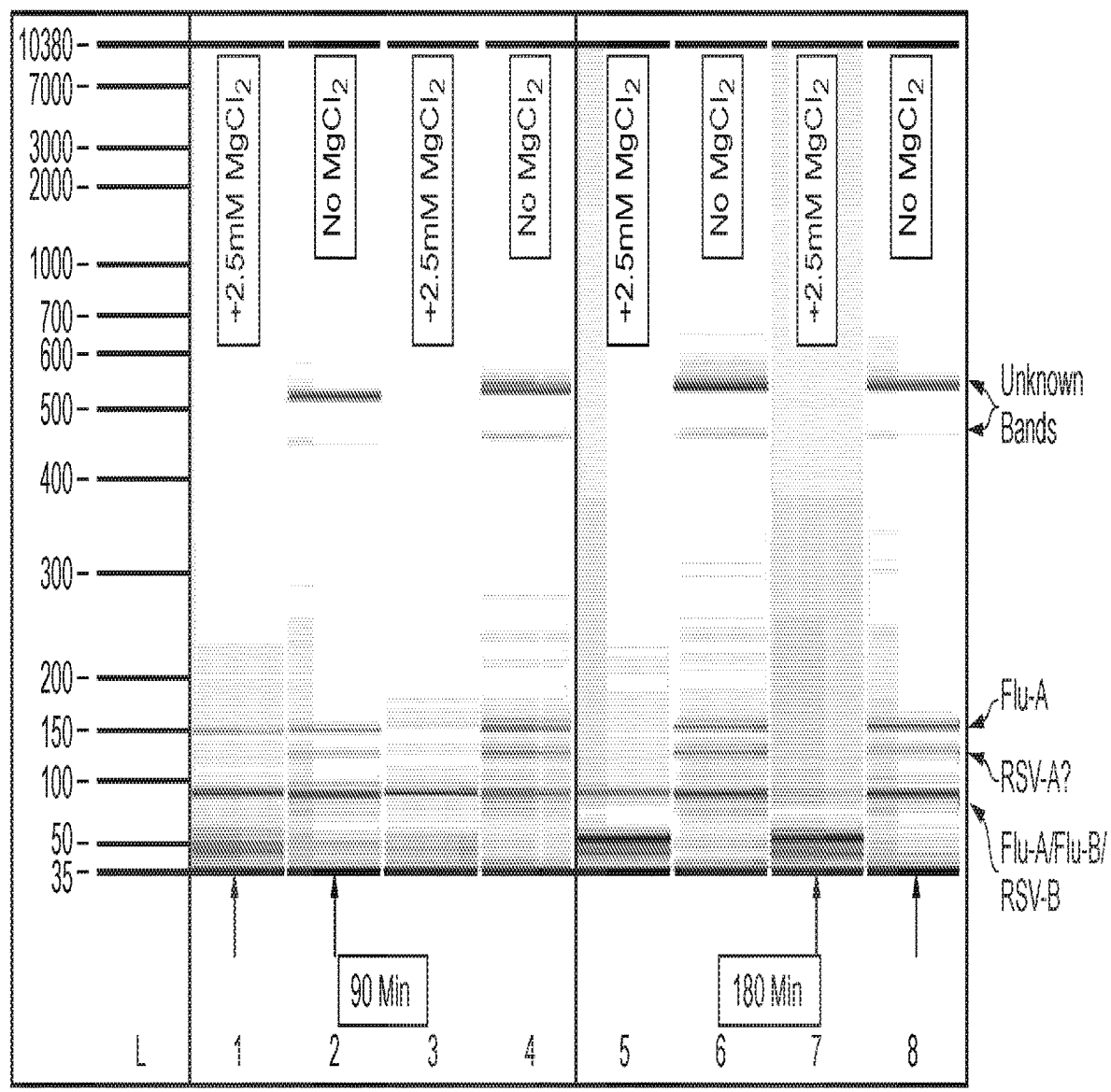

FIG. 4 is a bioanalyzer gel-like image showing the effect that incubating the pre-dried bulk reagent in the presence or absence of $MgCl_2$ has on a subsequent nucleic acid multiplex amplification assay against Influenza A, Influenza B and Respiratory Syncytial Virus (RSV). Bulk reagent that was devoid of $MgCl_2$, and in turn dried to generate a dried composition devoid of $MgCl_2$, had the $MgCl_2$ added before the amplification reaction. Reagents incubated with $MgCl_2$ in the pre-dried bulk reagent show non-specific, low molecular weight amplification (smear), indicating the formation of a low molecular weight side-product indicating primer-dimers and other spurious events that subsequently lead to lower amplification efficiency of the intended nucleic acid target. Reagents incubated without $MgCl_2$ in the pre-dried bulk reagent show stronger distinct target bands and low side-product formation in comparison to the conditions wherein $MgCl_2$ is present in the pre-dried bulk reagent, indicating that stability is improved in the bulk formulation master mix by excluding $MgCl_2$. Lane 1 is the result obtained after 90 minutes on an ice chilled plate with 2.5 mM $MgCl_2$ in the master mix; lane 2 is the result obtained after 90 minutes on ice plate with no $MgCl_2$ in the master mix; lane 3 is the result obtained after 90 minutes at room temperature on a pre-chilled plate with 2.5 mM $MgCl_2$ in the master mix; lane 4 is the result obtained after 90 minutes at room temperature on pre chilled plate with no $MgCl_2$ in the master mix; lane 5 is the result obtained after 180 minutes on an ice chilled plate with 2.5 mM $MgCl_2$ in the master mix; lane 6 is the result obtained after 180 minutes on an ice chilled plate with no $MgCl_2$ in the master mix; lane 7 is the result obtained after 180 minutes at room temperature with 2.5 mM $MgCl_2$ in the master mix; lane 8 is the result obtained after 180 minutes at room temperature with no $MgCl_2$ in the master mix.

Figure 5:
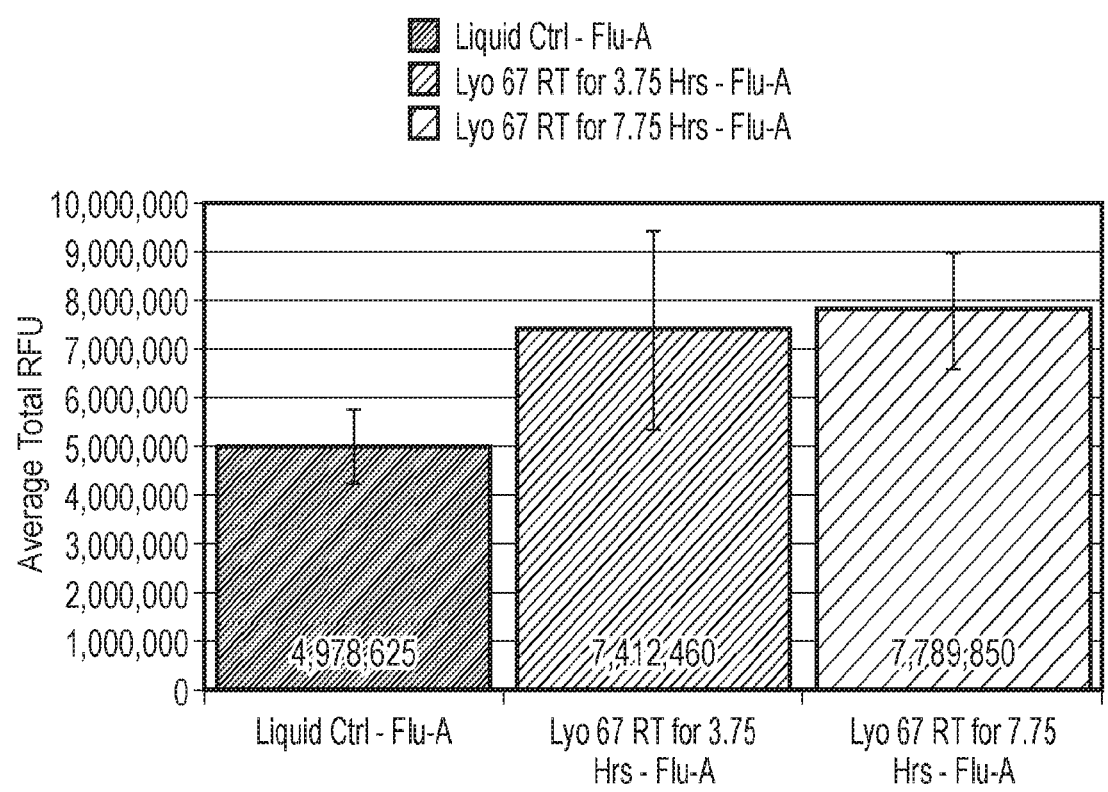

FIG. 5 shows the longer stability of the bulk formulations without $MgCl_2$, using Influenza A as a marker. Amplification response, measured as Relative Fluorescence Units (RFU) of bulk reagents incubated at room temperature for 3.75 and 7.75 hours were compared to a fresh liquid control, confirming stability of the bulk reagent at room temperature for more than 7.75 hours when $MgCl_2$ is excluded from the master mix.

Figure 6:
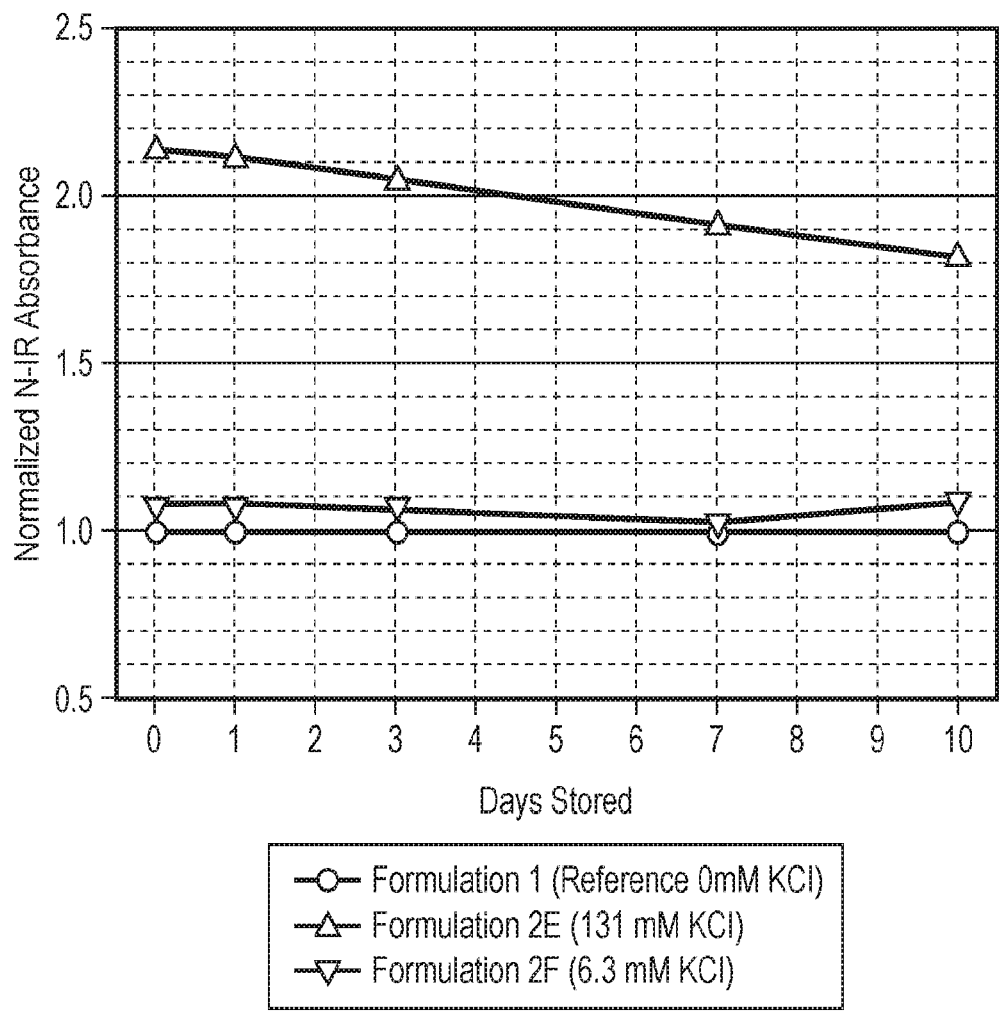

FIG. 6 shows average residual moisture of lyophilized reagent measured as relative absorbance of three formulations as determined by Fourier Transform near-infrared (FT-nIR) spectroscopy at a spatial wave length of 5170 cm$^{-1}$ ($A^{5170}$).

Figure 7:
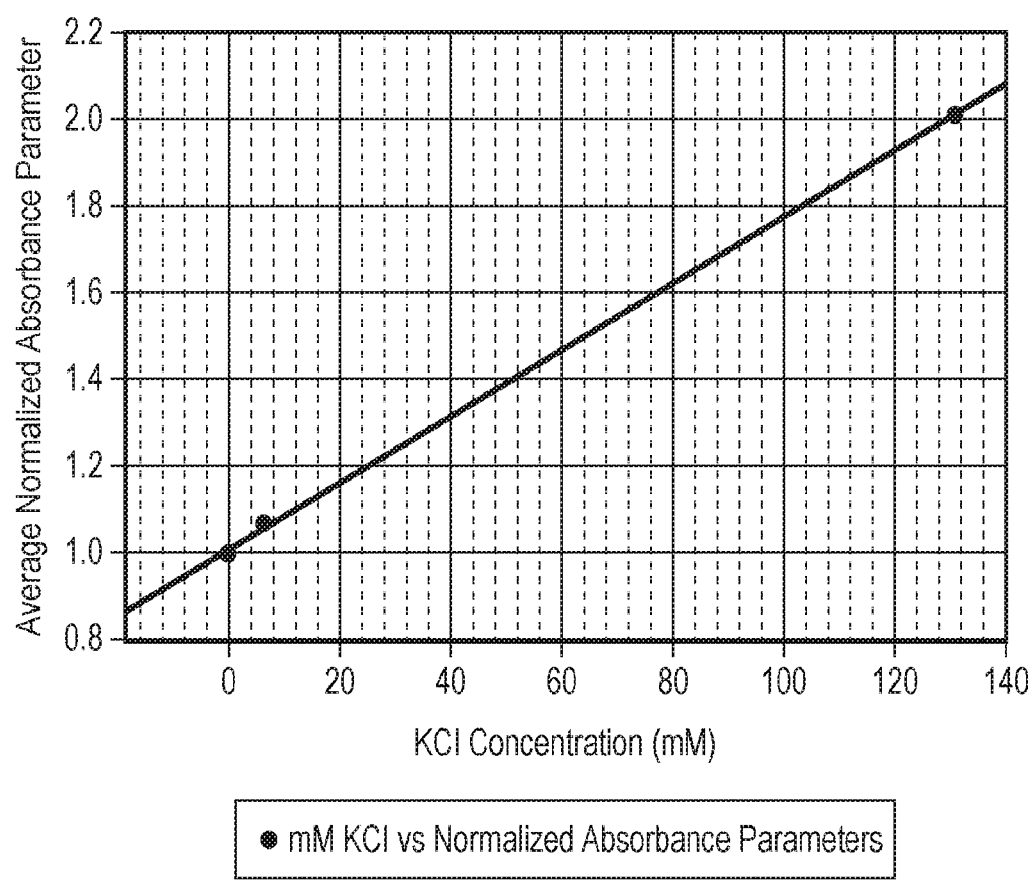

FIG. 7 shows the impact of KCl concentration on residual moisture, measured as absorbance.

DEFINITIONS

The term "about" indicates insubstantial variation in a quantity of a component of a composition not having any significant effect on the activity or stability of the composition.

A "bulking agent" provides a matrix for the deposit of proteins and other reagents during drying and storage. (Carpenter et al (2002) Rational design of stable lyophilized protein formulations. Kluwer Academic/Plenum, New York, pp. 109-133). Bulking agents can be used to form a product "cake" or other structure, and can prevent protein from being lost from the vial during drying and increase protein stability.

A chelating agent is an agent that sequesters divalent ions, including divalent ions such as $Mg^{2+}$ ions or $Mn^{2+}$ ions which are required for enzyme activity.

The terms "lyophilization," "lyophilized," and "freeze-dried" refer to a process by which the material to be dried is first frozen and then the ice or frozen solvent is removed by sublimation in a vacuum environment.

The term "stringent" in reference to nucleic acid hybridization (including "stringent hybridization conditions" or "stringent conditions") refers to conditions where a specific oligonucleotide is able to hybridize with its target nucleic acids over other nucleic acids present in the test sample. It will be appreciated that these conditions may vary depending upon factors including the GC content and length of the oligonucleotide, the hybridization temperature, the composition of the hybridization reagent or solution, and the degree of hybridization specificity sought. Appropriate hybridization conditions are well known in the art for probes, amplification oligonucleotides, target capture oligonucleotides, blockers and other oligonucleotides; may be predicted based on sequence composition; or may be determined by using routine testing methods (e.g., Sambrook et al., *Molecular Cloning, A Laboratory Manual*, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57).

An amplification oligomer is a primer or promoter primer that can support template-dependent replication of a target nucleic acid. An amplication oligomer pair is a pair of such oligomers that support template dependent replication of opposing strands of a template. Multiplex amplification is amplification performed simultaneously with multiple amplification oligomer pairs.

A probe is an oligonucleotide that can hybridize to an amplification product to reveal presence or amount of the amplification product. Such probes often incorporate a molecule giving a fluorescent or other detectable signal in which case they are referred to as detectably labelled probes.

A primer-probe set is a combination of primers and probe configured for generating an amplification product from a template nucleic acid and detecting an amplification product from a template nucleic acid.

As used herein, a "label" refers to a moiety or compound joined directly or indirectly to a probe or to a dNTP that is detectable or leads to a detectable signal. Direct labelling can occur through bonds or interactions that link the label to a probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. Synthesis and methods of attaching labels to nucleic acids and detecting labels are well known (e.g., Sambrook et al., *Molecular Cloning, A Laboratory Manual*, 2nd ed. (Cold Spring Harbor Laboratory Press, Cold Spring Harbor, NY, 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

"Reconstitution time" is the time that is required to rehydrate a dried formulation with a solution to result in a solution. Preferably, but not always depending on the formulation, a reconstituted solution is one that is free of particles or turbidity to the naked eye.

Relative Fluorescence Units (RFU) are a measure of amplification product, and by implication a nucleic acid analyte in a sample that gives rise to the amplification product.

Ct refers is the number of cycles that was required to reach the exponential phase in a real time PCR. Ct is inversely related to the amount of analyte in a sample.

Positivity, when in reference to assay reaction results, refers experimental data generated from a sample and that has crossed over a threshold value (such as an RFU value). Threshold values are set by a user, and are typically determined based on emperical data obtained for a given assay. Typically for nucleic acid amplification assays a threshold value is set so that positive samples have crossed the threshold and moved into an exponential growth phase of the assay. Positivity values are in reference a single sample that has crossed the threshold value or to the percentage of a plurality of samples that have crossed the threshold value. For example, when the plurality of samples is twelve samples, and when the number of samples crossing over was determined to be six, positivity is "50%." The threshold value is often set to exclude background values.

A "single unit dose" or "SUD" refers to a volume of a reaction mixture that is used to perform a molecular assay on a single sample. A single unit dose can be in liquid form or in dried form. By way of example, a single unit dose can be a dried pellet containing reagents useful for the amplification of a single sample in a single vessel.

LOD is limit of detection of an analyte. LOD+1 is the LOD that the user has detected plus one log. In other words, LOD+1 is ten times the number of analytes that is the LOD.

Ranges of values herein are inclusive of all whole numbers therein and, when practical, all partial numbers therein. For example, a range of pH values from pH 2.0 to pH 5.0 would be inclusive of all whole and partial numbers therein, while a length range for an oligonucleotide from 23 to 30 contiguous nucleotides would only be inclusive of all whole numbers therein.

Whenever the disclosure refers to a composition comprising specified components, the disclosure should be understood as also disclosing compositions consisting of or consisting essentially of the specified components.

DETAILED DESCRIPTION

I. General

The present disclosure is premised in part on the insight that instability of prior lyophilized kits for performing molecular assays such as nucleic acid amplifications is due to the presence of inorganic salts. These salts can result in undesired hybridization products or other byproducts before, during and after drying. These salts also make a dried composition hygroscopic such that the composition absorbs water from its surrounding environment. Thus, because of the salt content in a dried composition, limited exposure to humidity, refrigeration or deep freeze storage and/or storage in the presence of a desiccant is required. The presence of water and salts causes the polymerase component of the dried composition to lose activity prematurely and can also facilitate hybridization of nucleic acids to each other. The presence of salts can also reduce the ability to prepare dried reagents, for example, by lyophilization. Conversely, the absence of salts in an enzyme containing composition is known to lead to denaturation of the enzyme component, thus making salt-free compositions of these enzymes also undesirable. The present disclosure has overcome these problems by drying bulk reagents for conducting nucleic acid based reaction mixture from bulk reagents essentially free of inorganic salts. Such salts are supplied on reconstitution of the dried composition. Contrary to expectation that inorganic salts are necessary for stability of polymerases, it has been found that nucleic acid based reaction mixtures dried essentially free of inorganic salt can be stored long term above freezing, with full or substantial retention of activity on reconstitution.

II. Bulk Reagents & Dried Pellets

Bulk reagents (sometimes referred to as prelyophilized mixtures, solutions, aqueous solutions or compositions) according to the disclosure typically include a polymerase, nucleotides for use in a nucleic acid based amplification reaction, an organic buffer, preferably Tris, and a bulking agent such as trehalose or raffinose or a combination thereof. Bulk reagents may or may not also include one or more nucleic acids. Bulk reagents may additionally include reverse transcriptase enzymes, chelators, and RNase inhibitors. The term bulk reagent is used in reference to an aqueous solution as described above, wherein the aqueous solution will be separated into two or more aliquots having substantially the same concentrations of reagents. Also, an aliquoted portion of the bulk reagent may be referred to as a bulk reagent. Regardless of the context, a bulk reagent is an aqueous solution as described herein.

Such bulk reagents are essentially free of inorganic salts meaning the concentration of inorganic salt individually and collectively is less than 7 mM and preferably less than 1 mM. Preferably, the concentration of $Mg^{2+}$ is less than 1 mM, less than 0.5 mM, less than 0.1 mM or less than 0.05 mM. Preferably, the concentration of $Na^+$ is less than 1 mM, less than 0.5 mM, less than 0.1 mM or less than 0.05 mM. Preferably, the concentration of $K^+$ is less than 1 mM, less than 0.5 mM, less than 0.1 mM or less than 0.05 mM. Preferably, the concentration of $Cl^-$ is less than 1 mM, less than 0.5 mM, less than 0.1 mM or less than 0.05 mM.

Preferably, the concentration of $Mg^{2+}$ is less than 1 mM and the concentration of $Na^+$ is less than 1 mM. Preferably, the concentration of $Mg^{2+}$ is less than 0.5 mM and the concentration of $Na^+$ is less than 0.5 mM. Preferably, the concentration of $Mg^{2+}$ is less than 0.1 mM and the concentration of $Na^+$ is less than 0.1 mM. Preferably, the concentration of $Mg^{2+}$ is less than 0.05 mM and the concentration of $Na^+$ is less than 0.05 mM.

Preferably, the concentration of $Mg^{2+}$ is less than 1 mM and the concentration of $K^+$ is less than 1 mM. Preferably, the concentration of $Mg^{2+}$ is less than 0.5 mM and the concentration of $K^+$ is less than 0.5 mM. Preferably, the concentration of $Mg^{2+}$ is less than 0.1 mM and the concentration of $K^+$ is less than 0.1 mM. Preferably, the concentration of $Mg^{2+}$ is less than 0.05 mM and the concentration of $K^+$ is less than 0.05 mM.

Preferably, the concentration of $Mg^{2+}$ is less than 1 mM and the concentration of $Cl^-$ is less than 1 mM. Preferably, the concentration of $Mg^{2+}$ is less than 0.5 mM and the concentration of $Cl^-$ is less than 0.5 mM. Preferably, the concentration of $Mg^{2+}$ is less than 0.1 mM and the concentration of $Cl^-$ is less than 0.1 mM. Preferably, the concentration of $Mg^{2+}$ is less than 0.05 mM and the concentration of $Cl^-$ is less than 0.05 mM.

Preferably, the concentration of $Na^+$ is less than 1 mM and the concentration of $K^+$ is less than 1 mM. Preferably, the concentration of $Na^+$ is less than 0.5 mM and the concentration of $K^+$ is less than 0.5 mM. Preferably, the concentration of $Na^+$ is less than 0.1 mM and the concentration of $K^+$ is less than 0.1 mM. Preferably, the concentration of $Na^+$ is less than 0.05 mM and the concentration of $K^+$ is less than 0.05 mM.

Preferably, the concentration of $Na^+$ is less than 1 mM and the concentration of $Cl^-$ is less than 1 mM. Preferably, the concentration of $Na^+$ is less than 0.5 mM and the concentration of $Cl^-$ is less than 0.5 mM. Preferably, the concentration of $Na^+$ is less than 0.1 mM and the concentration of $Cl^-$ is less than 0.1 mM. Preferably, the concentration of $Na^+$ is less than 0.05 mM and the concentration of $Cl^-$ is less than 0.05 mM.

Preferably, the concentration of $K^+$ is less than 1 mM and the concentration of $Cl^-$ is less than 1 mM. Preferably, the concentration of $K^+$ is less than 0.5 mM and the concentration of $Cl^-$ is less than 0.5 mM. Preferably, the concentration of $K^+$ is less than 0.1 mM and the concentration of $Cl^-$ is less than 0.1 mM. Preferably, the concentration of $K^+$ is less than 0.05 mM and the concentration of $Cl^-$ is less than 0.05 mM.

Preferably, the concentration of $Mg^{2+}$ is less than 1 mM and the concentration of $Na^+$ is less than 1 mM and the concentration of $K^+$ is less than 1 mM. Preferably, the concentration of $Mg^{2+}$ is less than 0.5 mM and the concentration of $Na^+$ is less than 0.5 mM and the concentration of $K^+$ is less than 0.5 mM. Preferably, the concentration of $Mg^{2+}$ is less than 0.1 mM and the concentration of $Na^+$ is less than 0.1 mM and the concentration of $K^+$ is less than 0.1 mM. Preferably, the concentration of $Mg^{2+}$ is less than 0.1 mM and the concentration of $Na^+$ is less than 0.1 mM and the concentration of $K^+$ is less than 0.1 mM. Preferably, the concentration of $Mg^{2+}$ is less than 0.05 mM and the concentration of $Na^+$ is less than 0.05 mM and the concentration of $K^+$ is less than 0.05 mM.

Preferably, the concentration of $Na^+$ is less than 1 mM and the concentration of $K^+$ is less than 1 mM and the concentration of $Cl^-$ is less than 1 mM. Preferably, the concentration of $Na^+$ is less than 0.5 mM and the concentration of $K^+$ is less than 0.5 mM and the concentration of $Cl^-$ is less than 0.5 mM. Preferably, the concentration of $Na^+$ is less than 0.1 mM and the concentration of $K^+$ is less than 0.1 mM and the concentration of $Cl^-$ is less than 0.1 mM. Preferably, the concentration of $Na^+$ is less than 0.1 mM and the concentration of $K^+$ is less than 0.1 mM and the concentration of $Cl^-$ is less than 0.1 mM. Preferably, the concentration of $Na^+$ is less than 0.05 mM and the concentration of $K^+$ is less than 0.05 mM and the concentration of $Cl^-$ is less than 0.05 mM.

Preferably, the concentration of $Mg^{2+}$ is less than 1 mM and the concentration of $K^+$ is less than 1 mM and the concentration of $Cl^-$ is less than 1 mM. Preferably, the concentration of $Mg^{2+}$ is less than 0.5 mM and the concentration of $K^+$ is less than 0.5 mM and the concentration of $Cl^-$ is less than 0.5 mM. Preferably, the concentration of $Mg^{2+}$ is less than 0.1 mM and the concentration of $K^+$ is less than 0.1 mM and the concentration of Cl− is less than 0.1 mM. Preferably, the concentration of Mg2+ is less than 0.1 mM and the concentration of K+ is less than 0.1 mM and the concentration of Cl− is less than 0.1 mM. Preferably, the concentration of Mg2+ is less than 0.05 mM and the concentration of K+ is less than 0.05 mM and the concentration of Cl− is less than 0.05 mM.

Preferably, the concentration of Mg2+ is less than 1 mM and the concentration of Na+ is less than 1 mM and the concentration of Cl− is less than 1 mM. Preferably, the concentration of Mg2+ is less than 0.5 mM and the concentration of Na+ is less than 0.5 mM and the concentration of Cl− is less than 0.5 mM. Preferably, the concentration of Mg2+ is less than 0.1 mM and the concentration of Na+ is less than 0.1 mM and the concentration of Cl− is less than 0.1 mM. Preferably, the concentration of Mg2+ is less than 0.1 mM and the concentration of Na+ is less than 0.1 mM and the concentration of Cl− is less than 0.1 mM. Preferably, the concentration of Mg2+ is less than 0.05 mM and the concentration of Na+ is less than 0.05 mM and the concentration of Cl− is less than 0.05 mM.

Preferably, the concentration of Mg2+ is less than 1 mM and the concentration of Na+ is less than 1 mM and the concentration of K+ is less than 1 mM and the concentration of Cl− is less than 1 mM. Preferably, the concentration of Mg2+ is less than 0.5 mM and the concentration of Na+ is less than 0.5 mM and the concentration of K+ is less than 0.5 mM and the concentration of Cl− is less than 0.5 mM. Preferably, the concentration of Mg2+ is less than 0.1 mM and the concentration of Na+ is less than 0.1 mM and the concentration of K+ is less than 0.1 mM and the concentration of Cl− is less than 0.1 mM. Preferably, the concentration of Mg2+ is less than 0.05 mM and the concentration of Na+ is less than 0.05 mM and the concentration of K+ is less than 0.05 mM and the concentration of Cl− is less than 0.05 mM.

Nucleotides for incorporation into an amplification reaction are typically provided as dNTPs. Exemplary concentrations for dNTPs are 0.1 to 0.3 mM of dATP; 0.1 to 0.3 mM of dGTP; 0.1 to 0.3 mM of dCTP; 0.2 to 0.6 mM of dTTP; 0.2 to 0.6 mM of dUTP; and preferably about 0.2 mM of dATP; about 0.2 mM of dGTP; about 0.2 mM of dCTP and 0.4 mM dTTP or dUTP. Nucleotides for incorporation into an amplification reaction can also be provided as labeled dNTPs, such as are useful for sequencing reactions.

Such mixtures can be customized for different types of amplification including PCR, RT-PCR and transcription mediated amplification by the choice of enzyme and other components.

DNA polymerase enzymes are commercially available or can be prepared by a user. One example of a polymerase enzyme is a Taq polymerase commercially available from Qiagen (Germantown, MD, cat #201203). Another example of a Taq polymerase is commercially available as GoTaq® G2 Flexi DNA polymerase (Promega, Madison, WI, cat #M7801). Other DNA polymerases that are commercially available include, but are not limited to, Tth DNA polymerase (e.g., Sigma-Aldrich, St. Louis, MO, cat #11480022001), and chimeric DNA polymerases such as Phusion® High-Fidelity DNA Polymerase (NEB, Ipswich, MA, cat #M0530S). Also commercially available are hot-start DNA polymerase enzymes. For example, a Taq polymerase is commercially available as GoTaq® Hot Start Polymerase (Promega, cat #M5001). The GoTaq® Hot Start polymerase is an antibody mediated hot start enzyme, where the Taq polymerase is bound to an antibody that blocks polymerase activity. The blocking antibody is denatured using high heat, thus during the initial heat step of a PCR reaction, the antibody is denatured and polymerase activity is restored. Various antibodies can be used with hot start method, for example, TAQSTART antibody (Clontech Laboratories, Mountain View, CA, cat #R028A). Similarly, other hot start polymerase enzymes are available, including chemically-mediated hot start polymerases. Equivalent polymerase and antibodies are available from a variety of commercial sources and, alternatively, can be prepared by the user.

Reverse transcriptase enzymes are commercially available or can be prepared by a user. Examples of commercially available reverse transcriptase include, but are not limited to, MMLV (Maloney Murine Leukemia Virus) reverse transcriptase & SuperScript® III Reverse Transcriptase (e.g., ThermoFisher Scientific, Carlsbad, CA, cat #s 28025-013 & 18080-044), MMLV RT (Sigma-Aldrich, cat #M1302), AMV Reverse Transcriptase (NEB, Ipswich, MA, cat #M0277S), and GoScript™ reverse transcriptase (Promega, cat #A50003). GoScript reverse transcriptase includes a reverse transcriptase and a set of reagents for synthesis of first-strand cDNA optimized for quantitative PCR amplification. Equivalent reverse transcriptase and reagents are available from various commercial sources and, alternatively, can be prepared by the user.

Exemplary concentrations for DNA polymerase enzyme in single unit doses are 0.01-1.0 U/µl. For example 0.32 U/µl, or 0.4 U/µl or 0.72 U/µl, or 0.32-0.4 U/µl, or 0.4-0.72 U/µl, or 0.05-0.3 U/µl, or 0.8-1.0 U/µl. One unit of DNA polymerase is defined as the amount of enzyme required to catalyze the incorporation of 10 nanomoles of dNTPs into acid-insoluble material in 30 minutes at 74° C. Exemplary concentrations of reverse transcriptase enzyme in single unit doses are 0.01 U/µl-1.0 U/µl. One unit of reverse transcriptase is defined as the amount of enzyme required to catalyze the transfer of 1 nmol of deoxynucleotide into acid-precipitable material in 10 minutes at 37° C.

A preferred organic buffer is Tris. Alternative organic buffers that can be incorporated into bulk reagents of the disclosure include phosphate, citrate, acetate, CHES, histidine, and Good's buffers, such as HEPES, MES, MOPS, tricine, and glycinamide, as well as buffer combinations. Other organic buffers include succinate, citrate, gluconate, phosphate, and the like. Preferred buffers are effective in a pH range from about 5.5 to about 7.0 or about 6.0 to about 7.5; preferably a pH of about 6.5. Examples of buffers that control the pH in this range include succinate (such as sodium succinate), gluconate, histidine, citrate and other organic acid buffers.

Preferred bulking agents are trehalose or raffinose or a combination thereof. Other bulking agents that can be used include sucrose, mannitol, trehalose plus mannitol, sucrose plus mannitol, sucrose plus glycine, and hydroxyethyl starch. See, Cleland et al (2001) *J. Pharm. Sci.* 90:310; Meyer et al (2009) *Eur. J. Pharm. Sci.* 38:29; Webb et al (2003) *J. Pharm. Sci.* 92:715; Garzon Rodrigues et al (2004) *J. Pharm. Sci.* 93:684; Qiu et al (2012) *Int. J. Pharmaceuticals.* 437:51; Van Dijk-Wolthuis et al (1997) *Polymer.* 38:6235 6242. Hydroxyethyl starch is classified as, hetastarch, hexastarch, pentastarch, and tetrastarch (see, e.g., WO2014/099198 of Chow). The bulking agent is preferably present at a concentration of 0.16 M to 0.32 M, or alternatively, at 0.04 to 0.12M, 0.08 to 0.16M, 0.12 to 0.20M, 0.16 to 0.24M, 0.20 to 0.28M, 0.24 to 0.32M, 0.28 to 0.36M, 0.32 to 0.40M, or any combination of said ranges, such as 0.08 to 0.24M.

Bulk reagents may include one more nucleic acids, such as, for example, amplification oligomers (e.g., primers, T7 promoter oligonucleotides), capture probes, detection probes, Taqman probes, hairpin detection probes, adaptors, hairpin adaptors, positive control template, and negative control template.

Optional additional components of a bulk reagents include RNase inhibitor, PCR reagents, detergents, zwitterionic detergents, anionic detergents, cationic detergents, non-ionic detergents, surfactants, primers, probes, template, chelating agent, methyl paraben, and propyl paraben. An exemplary concentration for methyl paraben is 0.01-0.024% by weight, for example about 0.016%, or alternatively, about 0.010%, about 0.014%, about 0.016%, about 0.020%, about 0.024%, and any ranges bordered by these values. An exemplary concentration range of propyl paraben is 0.002-0.016% or 0.008%, or alternatively, about 0.002%, about 0.004%, about 0.006%, about 0.008%, about 0.010%, about 0.012%, about 0.014%, about 0.016% or any range bordered by these values. One unit is defined as the amount of RNasin® Ribonuclease Inhibitor required to inhibit the activity of 5 ng of ribonuclease A by 50%. Activity is measured by the inhibition of hydrolysis of cytidine 2',3'-cyclic monophosphate by ribonuclease A.

Chelating agents include one or more of EDTA (ethylenediaminetetraacetic acid), EGTA (ethylene glycol-bis(β-aminoethyl ether)-N,N,N',N'-tetraacetic acid), EDDS (ethylenediamine-N,N'-disuccinic acid), MGDA (methylglycindiacetic acid), and DTPA (diethylene triamine pentaacetic acid). Exemplary concentrations for chelating agents are from 1.0 mM-2.5 mM.

RNase inhibitor proteins are native and recombinant are 50 kDa proteins that inhibit RNase A family and human placental RNases by noncovalently binding to RNases in a 1:1 ratio (Promega Corp., Madison, WI). See, Botella-Estrada et al (2001) *Cancer Gene Ther.* 8:278; Polakowski et al (1992) *EXS.* 61:428. RNase inhibitor proteins can be either a recombinant or a native protein. Exemplary concentrations of RNase inhibitor about 0.04 U/µl to about 0.4 U/µl.

Bulk reagents can contain detergent at low concentration. Detergents include ionic (cationic or anionic), non-ionic and zwitterionic detergents available from a number of commercial vendors (e.g., Geno Technology, Inc., St. Louis, MO). Examples include, but are not limited to, lithium lauryl sulfate, amprolium hydrochloride, benzalkonium chloride, choline p-toluenesulfonate salt, dodecyltrimethylammonium chloride, 3-[(3-Cholamidopropyl)dimethylammonio]-1-propanesulfonate, ethylhexadecyldimethylammonium bromide, hexadecylpyridinium chloride, hexadecyltrimethylammonium chloride, sodium dodecyl sulfate, hexadecyltrimethylammonium p-toluenesulfonate, Iuviquat™, methylbenzethonium chloride, myristyltrimethylammonium bromide, N,N',N'-Polyoxyethylene (10)-N-tallow-1,3-diaminopropane liquid, oxyphenonium bromide, tetraheptylammonium bromide, tetrakis(decyl) ammonium bromide, tricaprylylmethylammonium chloride, Amidosulfobetaine-16, tridodecylmethylammonium chloride, trimethyloctadecylammonium bromide, Nonidet P-40R, Tween-20R, Tween-80R, Brij-35R, Triton X-100R.

Exemplary volumes of a bulk reagents include about 1 µl, about 5 µl, about 10 µl, about 20 µl, about 24 µl, about 50 µl, about 100 µl, about 200 µl, about 300 µl, about 400 µl, about 500 µl about 600 µl, about 700 µl, about 800 µl, about 900 µl, about 1,000 µl (1 mL), about 2 mL, about 5 mL, about 10 mL, about 20 mL, about 50 mL, and so on. Exemplary volumes of a single unit dose include from about 1 µl to about 1 mL. Reconstituted dried compositions can be formed at the same liquid volume as used to form the dried composition, at a lower volume, or at a greater volume. A lower volume can be about 90%, about 80%, about 60%, about 40%, about 20%, about 10%, or about 5%, relative to the bulk reagents. A greater volume can be about 120%, 140%, 160%, 180%, 200% (2-fold), about 4-fold, about 6-fold, about 8-fold, about 10-fold, about 20-fold, that of the bulk reagents.

A sample to be analyzed can be added to the bulk reagents either before reconstitution, at the same time as reconstitution, or after reconstitution. In a preferred embodiment, the entire dried composition after reconstitution is used for combining with sample, and here the relative volumes of reconstitution solution/sample can be, for example, about 9.9/0.1, 9.8/0.2, 9.5/0.5, 9/1, 8/2, 7/3, 6/4, 5/5, and so on.

Unless otherwise specified, concentrations of reagents in bulk reagents can be for example, 0.0% (an omitted reagent), 0.001%, 0.004%, 0.008%, 0.0012%, 0.0016%, 0.0020%, 0.0030%, 0.0040%, 0.0050%, 0.0060%, 0.0080%, 0.01%, 0.02%, 0.04%, 0.06%, 0.1%, 0.2%, 0.3%, 0.4%, 0.5%, 0.6%, 0.8%, 1%, 2%, 3%, 4%, 5%, and the like. Also provided are reagents that are at "about" the above concentrations, less than the above concentrations, more than the above concentrations, and ranges involving any two of the above concentrations.

An exemplary bulk reagent composition has 0.1-0.3 mM and more preferably 0.2 mM dATP, dGTP and dCTP, as well as 0.2-0.6 mM and more preferably 0.4 mM, dUTP or dTTP, and 0.3-0.8 U/µL polymerase. In some compositions, the polymerase is a hot start Taq polymerase. In some compositions, the polymerase is a GoTaq® MDx Hot Start polymerase. Some compositions also include RNAasin® RNAase inhibitor at 0.12-0.20 U/µL. Some compositions also include EDTA, optionally at 1.5-2.0 mM. Such a composition also includes trehalose at 0.16-0.32 M, EDTA at 1.5-2.0 mM and the polymerase is Taq at 0.3-0.45 U/µL.

The present disclosure provides reagents for PCR reactions, including real-time PCR reactions. (*Real-time PCR Handbook, Life Technologies* (2014); Kutyavin et al (2000) *Nucleic Acids Res.* 28:655; Afonina et al (2002) *Biotechniques.* 32:940). In real-time PCR, magnesium salt is typically used at a final concentration 3-6 mM (*Real-time PCR Handbook,* supra). In some embodiments, the disclosure provides reagents for multiplex PCR reactions, that is, where a plurality of primer pairs is provided for the amplification and detection of a plurality of targets. The disclosure provides primers and probes for PCR reactions. Primers and/or probes comprise target hybridizing sequences, and can further comprise one or more of non-target hybridizing sequences, nucleotide analogs, detectable moieties, and non-nucleotide linkers (see e.g., WO) 2010/151566 and WO 2013/126793) Thermocyclers are available (Applied Biosystems ProFlex® PCR System and Veriti® Thermal Cycler). Gel scanners for quantifying PCR products are available (Agilent® 2100 Bioanalyzer®, Bio-Rad® densitometer).

After formation of a bulk reagent it may be left at room temperature for a significant period before drying. The period can be for up to 8 hr before drying step is initiated, or alternatively, for up to 1 hr, up to 2 hr, up to 4 hr, up to 6 hr, up to 10 hr, up to 12 hr, up to 14 hr, before drying step is initiated. Inclusion of salts in the bulk reagent results in undesired hybridization products and other by-products during this incubation period. Such undesired hybridization and by-products are reduced or eliminated by forming the bulk reagent composition with an inorganic salt concentration of 7 mM or less, for example, essentially without inorganic salt, in accordance with the present disclosure.

The presence of inorganic salts in a bulk reagent results in one or more of the following undesirable properties. Nucleic acids may hybridize together, the hybridization being stimulated by the presence of inorganic salts such as potassium, sodium, manganese, magnesium and/or chloride. Also in the presence of inorganic salts like manganese and magnesium, undesirable enzyme activity can occur, such as polymerase processivity and/or the depletion of triphosphates. Such undesired activity can occur with non-hot-start enzymes and with hot-start enzymes. As a result of nucleic acid hybridization and enzyme activity in the presence of salt, undesired side-products may start to form. Additionally, inorganic salts are hygroscopic and will draw moisture into a dried pellet. Rehydration of the dried pellet reduces storage stability, enzyme stability, and allows for additional spurious side product formation.

A dried pellet can contain regents to provide one single unit dose (SUD), or optionally, two or more SUDs. A single unit dose is a collection of regents necessary to perform an amplification and/or a detection reaction on nor more than a single sample. Single unit dose can refer to a liquid reagent or a dried pellet. It is notable that a single unit dose, as referred to herein, need not contain all of the reagents necessary to perform an amplification and/or detection reaction on a single sample. A single unit dose may lack a reagent needed for performing amplification and/or detection reactions. Similarly, a single unit dose may contain an insufficient amount of a reagent for performing amplification and/or detection reactions. By way of example only, a dried single unit dose pellet may comprise adequate units of Taq polymerase for performing an amplification reaction, but may contain no magnesium. In certain embodiments, EDTA may be added to the dried single unit dose pellet to chelate excess divalent ions (e.g., magnesium and/or manganese) that may be present in a pellet or added by a reconstitution solution. In an example such as this, the magnesium and/or manganese can be added subsequently to the dried single unit dose pellet, such as by way of a reconstitution solution. Also by way of example only, a dried single unit dose may comprise an inadequate amount of dNTPs for performing an amplification reaction. In an example such as this, the remainder of the dNTPs can be added to the dried single unit dose pellet, such as by way of a reconstitution solution. Ordinarily skilled artisans in possession of this disclosure will readily generate SUDs and dried pellet SUDs with varied compositions, as these examples are non limiting.

In a preferred embodiment, a bulk reagent comprises 7 mM or less of inorganic salt content, more preferably 6 mM or less of inorganic salt content, more preferably 5 mM or less of inorganic salt content, more preferably 4 mM or less of inorganic salt content, more preferably 3 mM or less of inorganic salt content, more preferably 2 mM or less of inorganic salt content, more preferably 1 mM or less of inorganic salt content, or more preferably 500 uM or less of inorganic salt content. Thus a preferred concentration range of inorganic salt in a bulk reagent is from about 0 mM to 7 mM inorganic salt content. Another preferred concentration range of inorganic salt in a bulk reagent is from about 0 mM to 6 mM inorganic salt content. Another preferred concentration range of inorganic salt in a bulk reagent is from about 0 mM to 7 mM inorganic salt content. Another preferred concentration range of inorganic salt in a bulk reagent is from about 0 mM to 4 mM inorganic salt content. Another preferred concentration range of inorganic salt in a bulk reagent is from about 0 mM to 3 mM inorganic salt content.

Another preferred concentration range of inorganic salt in a bulk reagent is from about 0 mM to 2 mM inorganic salt content. Another preferred concentration range of inorganic salt in a bulk reagent is from about 0 mM to 1 mM inorganic salt content. Another preferred concentration range of inorganic salt in a bulk reagent is from about 0 mM to 0.5 mM inorganic salt content. Common inorganic salts for amplification and detection reaction mixtures include one or more of sodium, potassium, manganese, magnesium and chloride, to name a few.

In one aspect, a bulk reagent comprises 5 mM or less of inorganic salt, and the inorganic salts are present in a mass per microliter of 0.373 µg/µl or less, or 0.332 µg/µl or less, or 0.292 µg/µl or less. In a further aspect, a bulk reagent comprises 5 mM or less of inorganic salt, and the sodium chloride is present at a mass per microliter of 0.292 µg/µl or less, of 0.146 µg/µl or less, or of 0.0 µg/µl. In a further aspect, a bulk reagent comprises 5 mM or less of inorganic salt, and the sodium is present at a mass per microliter of 0.115 µg/µl or less, of 0.057 µg/µl or less, or of 0.0 µg/µl. In a further aspect, a bulk reagent comprises 5 mM or less of inorganic salt, and the potassium chloride is present at a mass per microliter of 0.373 µg/µl or less, of 0.186 µg/µl or less, or of 0.0 µg/µl. In a further aspect, a bulk reagent comprises 5 mM or less of inorganic salt, and the potassium is present at a mass per microliter of 0.196 µg/µl or less, of 0.098 µg/µl or less, or of 0.0 µg/µl. In a further aspect, a bulk reagent comprises 5 mM or less of inorganic salt, and the chloride is present at a mass per microliter of 0.355 µg/µl or less, of 0.178 µg/µl or less, of 0.089 µg/µl or less, or of 0.0 µg/µl.

In another aspect, a bulk reagent comprises 5 mM or less of inorganic salt, and the sodium chloride is present at a mass per microliter of 0.292 µg/µl or less, of 0.146 µg/µl or less, or of 0.0 µg/µl and the sodium is present at a mass per microliter of 0.115 µg/µl or less, of 0.057 µg/µl or less, or of 0.0 µg/µl and the potassium chloride is present at a mass per microliter of 0.373 µg/µl or less, of 0.186 µg/µl or less, or of 0.0 µg/µl and the potassium is present at a mass per microliter of 0.196 µg/µl or less, of 0.098 µg/µl or less, or of 0.0 µg/µl and the chloride is present at a mass per microliter of 0.355 µg/µl or less, of 0.178 µg/µl or less, of 0.089 µg/µl or less, or of 0.0 µg/µl.

In a further aspect, a dried pellet is made from drying a liquid bulk reagent comprising 5 mM or less of an inorganic salt, and the percent mass of the inorganic salt to the mass of the pellet is 0.311% or less, 0.277% or less, or 0.244% or less. In a further aspect, there is provided a vessel that contains a dried single unit dose pellet with a percent mass of inorganic salt to mass of pellet of 0.311% or less, 0.277% or less, or 0.244% or less. In a further aspect, there is provided a multiwell plate comprising one or more wells, wherein each of the one or more wells contains a dried single unit dose pellet that contains a percent mass of inorganic salt to mass of pellet of 0.311% or less, 0.277% or less, or 0.244% or less.

In one aspect, a bulk reagent comprises 4 mM or less of inorganic salt, the inorganic salts are present in a mass per microliter of 0.298 µg/µl or less, or 0.266 µg/µl or less, or 0.234 µg/µl or less. In a further aspect, a bulk reagent comprises 4 mM or less of inorganic salt, and the sodium chloride is present at a mass per microliter of 0.234 µg/µl or less, of 0.117 µg/µl or less, or of 0.0 µg/µl. In a further aspect, a bulk reagent comprises 4 mM or less of inorganic salt, and the sodium is present at a mass per microliter of 0.092 µg/µl or less, of 0.046 µg/µl or less, or of 0.0 µg/µl. In a further aspect, a bulk reagent comprises 4 mM or less of inorganic salt, and the potassium chloride is present at a mass per microliter of 0.298 µg/µl or less, of 0.149 µg/µl or less, or of 0.0 µg/µl. In a further aspect, a bulk reagent comprises 4 mM or less of inorganic salt, and the potassium is present at a mass per microliter of 0.156 µg/µl or less, of 0.078 µg/µl or less, or of 0.0 µg/µl. In a further aspect, a bulk reagent comprises 4 mM or less of inorganic salt, and the chloride is present at a mass per microliter of 0.284 µg/µl or less, of 0.142 µg/µl or less, of 0.071 µg/µl or less, or of 0.0 µg/µl.

In another aspect, a bulk reagent comprises 4 mM or less of inorganic salt, and the sodium chloride is present at a mass per microliter of 0.234 µg/µl or less, of 0.117 µg/µl or less, or of 0.0 µg/µl and the sodium is present at a mass per microliter of 0.092 µg/µl or less, of 0.046 µg/µl or less, or of 0.0 µg/µl and the potassium chloride is present at a mass per microliter of 0.298 µg/µl or less, of 0.149 µg/µl or less, or of 0.0 µg/µl and the potassium is present at a mass per microliter of 0.156 µg/µl or less, of 0.078 µg/µl or less, or of 0.0 µg/µl and the chloride is present at a mass per microliter of 0.284 µg/µl or less, of 0.142 µg/µl or less, of 0.071 µg/µl or less, or of 0.0 µg/µl.

In a further aspect, a dried pellet is made from drying a liquid bulk reagent comprising 4 mM or less of an inorganic salt, and the percent mass of the inorganic salt to the mass of the pellet is 0.249% or less, 0.222% or less, or 0.195% or less. In a further aspect, there is provided a vessel that contains a dried single unit dose pellet with a percent mass of inorganic salt to mass of pellet of 0.249% or less, 0.222% or less, or 0.195% or less. In a further aspect, there is provided a multiwell plate comprising one or more wells, wherein each of the one or more wells contains a dried single unit dose pellet that contains a percent mass of inorganic salt to mass of pellet of 0.249% or less, 0.222% or less, or 0.195% or less.

In one aspect, a bulk reagent comprises 3 mM or less of inorganic salt, the inorganic salts are present in a mass per microliter of 0.224 µg/µl or less, or 0.199 µg/µl or less, or 0.175 µg/µl or less. In a further aspect, a bulk reagent comprises 3 mM or less of inorganic salt, and the sodium chloride is present at a mass per microliter of 0.175 µg/µl or less, of 0.088 µg/µl or less, or of 0.0 µg/µl. In a further aspect, a bulk reagent comprises 3 mM or less of inorganic salt, and the sodium is present at a mass per microliter of 0.069 µg/µl or less, of 0.034 µg/µl or less, or of 0.0 µg/µl. In a further aspect, a bulk reagent comprises 3 mM or less of inorganic salt, and the potassium chloride is present at a mass per microliter of 0.224 µg/µl or less, of 0.112 µg/µl or less, or of 0.0 µg/µl. In a further aspect, a bulk reagent comprises 3 mM or less of inorganic salt, and the potassium is present at a mass per microliter of 0.117 µg/µl or less, of 0.059 µg/µl or less, or of 0.0 µg/µl. In a further aspect, a bulk reagent comprises 3 mM or less of inorganic salt, and the chloride is present at a mass per microliter of 0.213 µg/µl or less, of 0.107 µg/µl or less, of 0.053 µg/µl or less, or of 0.0 µg/µl.

In another aspect, a bulk reagent comprises 3 mM or less of inorganic salt, and the sodium chloride is present at a mass per microliter of 0.175 µg/µl or less, of 0.088 µg/µl or less, or of 0.0 µg/µl and the sodium is present at a mass per microliter of 0.069 µg/µl or less, of 0.034 µg/µl or less, or of 0.0 µg/µl and the potassium chloride is present at a mass per microliter of 0.224 µg/µl or less, of 0.112 µg/µl or less, or of 0.0 µg/µl and the potassium is present at a mass per microliter of 0.117 µg/µl or less, of 0.059 µg/µl or less, or of 0.0 µg/µl and the chloride is present at a mass per microliter of 0.213 µg/µl or less, of 0.107 µg/µl or less, of 0.053 µg/µl or less, or of 0.0 µg/µl.

In a further aspect, a dried pellet is made from drying a liquid bulk reagent comprising 3 mM or less of an inorganic salt, and the percent mass of the inorganic salt to the mass of the pellet is 0.186% or less, 0.166% or less, or 0.146% or less. In a further aspect, there is provided a vessel that contains a dried single unit dose pellet with a percent mass of inorganic salt to mass of pellet of 0.186% or less, 0.166% or less, or 0.146% or less. In a further aspect, there is provided a multiwell plate comprising one or more wells, wherein each of the one or more wells contains a dried single unit dose pellet that contains a percent mass of inorganic salt to mass of pellet of 0.186% or less, 0.166% or less, or 0.146% or less.

In one aspect, a bulk reagent comprises 2 mM or less of inorganic salt, the inorganic salts are present in a mass per microliter of 0.149 µg/µl or less, or 0.133 µg/µl or less, or 0.117 µg/µl or less. In a further aspect, a bulk reagent comprises 2 mM or less of inorganic salt, and the sodium chloride is present at a mass per microliter of 0.117 µg/µl or less, of 0.058 µg/µl or less, or of 0.0 µg/µl. In a further aspect, a bulk reagent comprises 2 mM or less of inorganic salt, and the sodium is present at a mass per microliter of 0.046 µg/µl or less, of 0.023 µg/µl or less, or of 0.0 µg/µl. In a further aspect, a bulk reagent comprises 2 mM or less of inorganic salt, and the potassium chloride is present at a mass per microliter of 0.149 µg/µl or less, of 0.075 µg/µl or less, or of 0.0 µg/µl. In a further aspect, a bulk reagent comprises 2 mM or less of inorganic salt, and the potassium is present at a mass per microliter of 0.078 µg/µl or less, of 0.039 µg/µl or less, or of 0.0 µg/µl. In a further aspect, a bulk reagent comprises 2 mM or less of inorganic salt, and the chloride is present at a mass per microliter of 0.142 µg/µl or less, of 0.071 µg/µl or less, of 0.036 µg/µl or less, or of 0.0 µg/µl.

In another aspect, a bulk reagent comprises 2 mM or less of inorganic salt, and the sodium chloride is present at a mass per microliter of 0.117 µg/µl or less, of 0.058 µg/µl or less, or of 0.0 µg/µl and the sodium is present at a mass per microliter of 0.046 µg/µl or less, of 0.023 µg/µl or less, or of 0.0 µg/µl and the potassium chloride is present at a mass per microliter of 0.149 µg/µl or less, of 0.075 µg/µl or less, or of 0.0 µg/µl and the potassium is present at a mass per microliter of 0.078 µg/µl or less, of 0.039 µg/µl or less, or of 0.0 µg/µl and the chloride is present at a mass per microliter of 0.142 µg/µl or less, of 0.071 µg/µl or less, of 0.036 µg/µl or less, or of 0.0 µg/µl.

In a further aspect, a dried pellet is made from drying a liquid bulk reagent comprising 2 mM or less of an inorganic salt, and the percent mass of the inorganic salt to the mass of the pellet is 0.124% or less, 0.111% or less, or 0.097% or less. In a further aspect, there is provided a vessel that contains a dried single unit dose pellet with a percent mass of inorganic salt to mass of pellet of 0.124% or less, 0.111% or less, or 0.097% or less. In a further aspect, there is provided a multiwell plate comprising one or more wells, wherein each of the one or more wells contains a dried single unit dose pellet that contains a percent mass of inorganic salt to mass of pellet of 0.124% or less, 0.111% or less, or 0.097% or less.

In one aspect, a bulk reagent comprises 1 mM or less of inorganic salt, the inorganic salts are present in a mass per microliter of 0.075 µg/µl or less, or 0.066 µg/µl or less, or 0.058 µg/µl or less. In a further aspect, a bulk reagent comprises 1 mM or less of inorganic salt, and the sodium chloride is present at a mass per microliter of 0.058 µg/µl or less, of 0.029 µg/µl or less, or of 0.0 µg/µl. In a further aspect, a bulk reagent comprises 1 mM or less of inorganic salt, and the sodium is present at a mass per microliter of 0.023 µg/µl or less, of 0.011 µg/µl or less, or of 0.0 µg/µl. In a further aspect, a bulk reagent comprises 1 mM or less of inorganic salt, and the potassium chloride is present at a mass per microliter of 0.075 µg/µl or less, of 0.037 µg/µl or less, or of 0.0 µg/µl. In a further aspect, a bulk reagent comprises 1 mM or less of inorganic salt, and the potassium is present at a mass per microliter of 0.039 µg/µl or less, of 0.020 µg/µl or less, or of 0.0 µg/µl. In a further aspect, a bulk reagent comprises 1 mM or less of inorganic salt, and the chloride is present at a mass per microliter of 0.071 µg/µl or less, of 0.036 µg/µl or less, of 0.018 µg/µl or less, or of 0.0 µg/µl.

In another aspect, a bulk reagent comprises 1 mM or less of inorganic salt, and the sodium chloride is present at a mass per microliter of 0.058 µg/µl or less, of 0.029 µg/µl or less, or of 0.0 µg/µl and the sodium is present at a mass per microliter of 0.023 µg/µl or less, of 0.011 µg/µl or less, or of 0.0 µg/µl and the potassium chloride is present at a mass per microliter of 0.075 µg/µl or less, of 0.037 µg/µl or less, or of 0.0 µg/µl and the potassium is present at a mass per microliter of 0.039 µg/µl or less, of 0.020 µg/µl or less, or of 0.0 µg/µl and the chloride is present at a mass per microliter of 0.071 µg/µl or less, of 0.036 µg/µl or less, of 0.018 µg/µl or less, or of 0.0 µg/µl.

In a further aspect, a dried pellet is made from drying a liquid bulk reagent comprising 1 mM or less of an inorganic salt, and the percent mass of the inorganic salt to the mass of the pellet is 0.062% or less, 0.055% or less, or 0.049% or less. In a further aspect, there is provided a vessel that contains a dried single unit dose pellet with a percent mass of inorganic salt to mass of pellet of 0.062% or less, 0.055% or less, or 0.049% or less. In a further aspect, there is provided a multiwell plate comprising one or more wells, wherein each of the one or more wells contains a dried single unit dose pellet that contains a percent mass of inorganic salt to mass of pellet of 0.062% or less, 0.055% or less, or 0.049% or less.

In one aspect, a bulk reagent comprises 500 uM or less of inorganic salt, the inorganic salts are present in a mass per microliter of 0.037 µg/µl or less, or 0.033 µg/µl or less, or 0.029 µg/µl or less. In a further aspect, a bulk reagent comprises 500 uM or less of inorganic salt, and the sodium chloride is present at a mass per microliter of 0.029 µg/µl or less, of 0.015 µg/µl or less, or of 0.0 µg/µl. In a further aspect, a bulk reagent comprises 500 uM or less of inorganic salt, and the sodium is present at a mass per microliter of 0.011 µg/µl or less, of 0.006 µg/µl or less, or of 0.0 µg/µl. In a further aspect, a bulk reagent comprises 500 uM or less of inorganic salt, and the potassium chloride is present at a mass per microliter of 0.037 µg/µl or less, of 0.019 µg/µl or less, or of 0.0 µg/µl. In a further aspect, a bulk reagent comprises 500 uM or less of inorganic salt, and the potassium is present at a mass per microliter of 0.020 µg/µl or less, of 0.010 µg/µl or less, or of 0.0 µg/µl. In a further aspect, a bulk reagent comprises 500 uM or less of inorganic salt, and the chloride is present at a mass per microliter of 0.036 µg/µl or less, of 0.018 µg/µl or less, of 0.009 µg/µl or less, or of 0.0 µg/µl.

In another aspect, a bulk reagent comprises 500 uM or less of inorganic salt, and the sodium chloride is present at a mass per microliter of 0.029 µg/µl or less, of 0.015 µg/µl or less, or of 0.0 µg/µl and the sodium is present at a mass per microliter of 0.011 µg/µl or less, of 0.006 µg/µl or less, or of 0.0 µg/µl and the potassium chloride is present at a mass per microliter of 0.037 µg/µl or less, of 0.019 µg/µl or less, or of 0.0 µg/µl and the potassium is present at a mass per microliter of 0.020 µg/µl or less, of 0.010 µg/µl or less, or of 0.0 µg/µl and the chloride is present at a mass per microliter of 0.036 µg/µl or less, of 0.018 µg/µl or less, of 0.009 µg/µl or less, or of 0.0 µg/µl.

In a further aspect, a dried pellet is made from drying a liquid bulk reagent comprising 500 uM or less of an inorganic salt, and the percent mass of the inorganic salt to the mass of the pellet is 0.031% or less, 0.028% or less, or 0.024% or less. In a further aspect, there is provided a vessel that contains a dried single unit dose pellet with a percent mass of inorganic salt to mass of pellet of 0.031% or less, 0.028% or less, or 0.024% or less. In a further aspect, there is provided a multiwell plate comprising one or more wells, wherein each of the one or more wells contains a dried single unit dose pellet that contains a percent mass of inorganic salt to mass of pellet of 0.031% or less, 0.028% or less, or 0.024% or less.

In one aspect, a bulk reagent comprises from about 5 mM to about 500 uM of inorganic salt, the inorganic salts are present in a mass per microliter from about 0.373 µg/µl to about 0.029 µg/µl. In a further aspect, a bulk reagent from about 5 mM to about 500 uM of inorganic salt, and the sodium chloride is present at a mass per microliter 0.292 µg/µl to about 0.029 µg/µl. In a further aspect, a bulk reagent from about 5 mM to about 500 uM of inorganic salt, and the sodium is present at a mass per microliter 0.115 µg/µl to about 0.006 µg/µl. In a further aspect, a bulk reagent comprises from about 5 mM to about 500 uM of inorganic salt, and the potassium chloride is present at a mass per microliter from about 0.373 µg/µl to about 0.019 µg/µl. In a further aspect, a bulk reagent from about 5 mM to about 500 uM of inorganic salt, and the potassium is present at a mass per microliter 0.196 µg/µl to about 0.010 µg/µl. In a further aspect, a bulk reagent from about 5 mM to about 500 uM of inorganic salt, and the chloride is present at a mass per microliter 0.355 µg/µl to about 0.009 µg/µl. In a further aspect, a bulk reagent comprises from about 5 mM to about 500 uM of inorganic salt, the inorganic salts are present in a mass per microliter from about 0.373 µg/µl to about 0.029 µg/µl, and the sodium chloride is present at a mass per microliter of about 0 µg/µl. In a further aspect, a bulk reagent comprises from about 5 mM to about 500 uM of inorganic salt, the inorganic salts are present in a mass per microliter from about 0.373 µg/µl to about 0.029 µg/µl, and the potassium chloride is present at a mass per microliter of about 0 µg/µl. In a further aspect, a dried pellet is made from drying a liquid bulk reagent comprising from 5 mM to 500 uM of an inorganic salt, and the percent mass of the inorganic salt to the mass of the pellet is from about 0.311% to 0.024%.

In a further aspect, a bulk reagent from about 5 mM to about 500 uM of inorganic salt, and the sodium chloride is present at a mass per microliter 0.292 µg/µl to about 0.029 µg/µl and the sodium is present at a mass per microliter 0.115 µg/µl to about 0.006 µg/µl and the potassium chloride is present at a mass per microliter from about 0.373 µg/µl to about 0.019 µg/µl and the potassium is present at a mass per microliter 0.196 µg/µl to about 0.010 µg/µl and the chloride is present at a mass per microliter 0.355 µg/µl to about 0.009 µg/µl.

In a further aspect, a bulk reagent comprises from about 5 mM to about 500 uM of inorganic salt, the inorganic salts are present in a mass per microliter from about 0.373 µg/µl to about 0.029 µg/µl, and the sodium chloride is present at a mass per microliter of about 0 µg/µl and the potassium chloride is present at a mass per microliter of about 0 µg/µl.

In a further aspect, a dried pellet is made from drying a liquid bulk reagent comprising from 5 mM to 500 uM of an inorganic salt, and the percent mass of the inorganic salt to the mass of the pellet is from about 0.311% to 0.024%, and the percent mass of the sodium chloride to mass of the pellet is about 0%, and/or the percent mass of the potassium chloride to mass of the pellet is about 0%. In a further aspect, there is provided a vessel that contains a dried single unit dose pellet with a percent mass of inorganic salt to mass of pellet is from about 0.311% to 0.024%, and the percent mass of the sodium chloride to mass of the pellet is about 0% and/or the percent mass of the potassium chloride to mass of the pellet is about 0%. In a further aspect, there is provided a multiwell plate comprising one or more wells, wherein each of the one or more wells contains a dried single unit dose pellet that contains a percent mass of inorganic salt to mass of pellet is from about 0.311% to 0.024%, and the percent mass of the sodium chloride to mass of the pellet is about 0% and/or the percent mass of the potassium chloride to mass of the pellet is about 0%.

In one embodiment there is provided a multiwell plate comprising one or more wells. In one aspect, a one or more wells comprise walls that are constructed from a material comprising a low moisture-vapor transmission rate, thermal conductivity, optical transparency, low autofluorescence, or a combination thereof. In one aspect, a one or more wells comprise walls that are cone shaped. In one aspect, a one or more wells comprise walls configured to fit into a PCR thermalcycler for performing a PCR amplification reaction on a reaction mixture contained within the well. In one aspect, a wells comprise walls configured to fit into a thermally conductive tube receiving area of a device for performing PCR, TMA, or other nucleic acid amplification reactions. In one aspect, a one or more wells comprise walls configured to fit into a heating block (see e.g. the dry blocks for use with digital dry block heaters available from Southern Labware, Cumming GA, as product SKUs BSH100G). In one aspect, a one or more wells of the multiwell plate comprises a opening for access to the chamber of the well. In one aspect, a one or more wells each comprises a cap to seal the opening of the associated well. In one aspect, an opening of each of the one or more wells is sealed with a cap that is a low moisture-vapor transmission rate foil. In one aspect, an opening of each of the one or more wells is sealed with a cap that is a low moisture-vapor transmission rate elastomeric substance. In one aspect, a multiwell plate comprises one or more wells as described herein, and wherein a chamber of the well contains a dried single unit dose pellet comprising a polymerase enzyme and an inorganic salt, wherein the percent mass of the inorganic salt to the mass of the pellet is from about 0.311% to 0.024%. In one aspect, a multiwell plate comprises one or more wells as described herein, and wherein a chamber of the well contains a dried single unit dose pellet comprising a reverse transcriptase enzyme and an inorganic salt, wherein the percent mass of the inorganic salt to the mass of the pellet is from about 0.311% to 0.024%. In one aspect, a multiwell plate comprises one or more wells as described herein, and wherein a chamber of the well contains a dried single unit dose pellet comprising a polymerase enzyme, a reverse transcriptase enzyme, and an inorganic salt, wherein the percent mass of the inorganic salt to the mass of the pellet is from about 0.311% to 0.024%.

Reaction mixtures can be assembled, and reactions can be carried out in automated sampling handling equipment, such as the Hologic® Panther instrument (Hologic, Inc., MA), which is a robotic device with pipetters, mixers, incubators, and wash stations, capable of conducting simultaneous multiple assays that use, for example, PCR reactions, transcription mediated amplification, and target capture hybridization.

III. Equipment and Methods for Drying

Bulk reagents can be lyophilized using standard methods and equipment. Freeze driers are available from, e.g., GEA Process Engineering, Columbia, MD. Contract freeze drying services are provided by a number of companies, (e.g., Biopharma Technology Ltd., Winchester, Hampshire, Great Britain and by BioPharma Solutions Sterile Contract Manufacturing, Baxter Healthcare Corp, Deerfield, IL). Guidance for lyophilization is available from a number of sources, (e.g., L. Rey, J. C. May (eds.) (2010) Freeze Drying Lyophilization of Pharmaceuticals and Biological Products, $3^{rd}$. ed. Informa Healthcare, *NY or Methods in Enzymology*, Vol. 22, Pages 33-39, Academic Press, New York (1971); or Freeze-Drying, E. W. Flosdorf, Rheinhold, New York (1949)). Optionally, oxygen content can be reduced during freeze-drying (Phillips et al (2001) *Biologics*. 19:219).

A variety of containers are suitable for drying. A container should be able to withstand the outside pressure when the container is sealed and stored under partial vacuum. The container should be made of a material that allows a reasonable transfer of heat from outside to inside. The size of the container is preferably such that the solution to be dried occupies not more than 20% of the total volume to avoid overflow.

Samples can be dried in separate vessels or a multispecimen vessels. A multi-specimen vessel means a contiguous vessel that can contain at least two specimens such that they can be stored and manipulated in parallel but separately. Standard formats for multispecimen receptacles include 6, 24, 96, 384 or 1536 wells. The volume of each well in an example of a 96 well format is about 300-400 microliters with a working volume of about 75-200 microliters. Volumes generally vary inversely with the number of wells, typically in a range between 1 nL and 10 mL for each well, although other sizes are also contemplated. Exemplary wells can have flat bottoms, round bottoms, or V-shaped bottoms among others. As used herein, a vessel is also referred to as a well. As used herein, a multispecimen vessel is also referred to as a multiwell plate. In addition, wells are sometimes further referred to as reaction wells. The term reaction well does not require that any reaction actually take place in the reaction well. Rather, the term is used to refer to a vessel or well that contains a reagent, and that may have no reaction therein, a partial reaction therein, or a full reaction therein.

A multiwell plate, in some embodiments herein, can undergo lyophilization to form a dried composition from an aqueous solution. Lyophilization may occur in a nest device (see copending International Patent Application No. PCT/US2016/045166). A nest is a container for holding the multiwell plate, the nest including vents which can be closed by a mechanism operable from outside a sealed lyophilization chamber. The nest containing the multiwell plate is placed within a lyophilization chamber with the one or more vents in the open position. The chamber is then sealed and a lyophilization atmosphere is applied throughout the chamber including the space within the nest. The one or more vents are then closed, thereby sealing the nest. The seal on the lyophilization chamber is later released and the nest containing the multiwell plate is removed. The nest may then be relocated and stored with the multiwell plate positioned therein until an operator is ready to use the lyophilized composition located therein or to reseal the multiwell plate containing the lyophilized specimens for further storage or sale. The wells of the multiwell plate can then be sealed substantially inhibiting entry of moisture from ambient air. The small amount of moisture entry into a sealed multiwell plate can be prevented by storing the sealed multiwell plate in a pouch containing desiccant. Similarly, separate vessels can undergo lyophilization, and can undergo lyophilization in a nest.

Other drying methods include spray drying, fluidized bed drying, dehumidifiers, and batch contact drying where a filter cake is dried at low temperature under vacuum to a free flowing dry product (N P Cheremisinoff (2000) *Handbook of Chemical Processing Equipment*, butterworth Heinemann, Boston, MA). Dehumidifies are available from Bry Air, Inc., Sunbury, Ohio, and DST Seibu Giken, Wyomissing, PA. Rotary dryers, conical dryers, and shelf dryers are available (McGill AirPressure LLC, Columbus, Ohio). In one embodiment, vacuum dryers remove moisture by exposing the materials to reduced pressure, where just enough heat is used to replace that lost through vaporization. Desiccants include silica gel desiccants, molecular sieve desiccants such as aluminosilicate and synthetic zeolite, and bentonite desiccants.

Reaction mixtures are preferably dried in the same vessel as that in which they will be reconstituted for use.

A lyophilized or otherwise dried formulation has a low water content, for example, under 5% water by weight, under 4%, under 3%, under 2%, under 1.0%, under 0.5%, under 0.2%, under 0.1%, under 0.05%, under 0.02%, under 0.01% by weight, and so on, or from under 5% water by weight to under 0.01% by weight, from under 4% to under 0.01%, from under 3% to under 0.01%, from under 2% to under 0.01%, from under 1.0% to under 0.01%, from under 0.5% to under 0.01%, from under 0.2% to under 0.01%, from under 0.1% to under 0.01%, from under 0.05% to under 0.01%, from under 0.02% to under 0.01%.

IV. Storage

Lyophilized or otherwise dried compositions are subject to storage before use. The period of storage can include a period of time in which the dried compositions are stored at room temperature exposed to ambient air. Such a period can be up to 3 hours, or alternatively, for up to 1.0 hour, up to 1.5 hours, up to 2.0 hours, up to 2.5 hours, up to 3.5 hours, up to 4.0 hours, up to 5.0 hours, up to 6.0 hours, up to 8.0 hours, or ranges of any of the times, such as from 90 min to 180 min. The absolute humidity during such storage can be at least 2.3 grams of water per cubic meter of air at 25° C., or alternatively, greater than 1.8, 2.0, 2.2, 2.4, 2.6, 2.8, 3.0 grams of water per cubic meter of air. Alternatively relative humidity can be e.g., about 10%, about 20%, about 30%, about 40%, about 50%, about 60%, about 70%, about 80%, about 90%, about 95% relative humidity. In certain embodiments, relative humidity can be about 10% and the period of storage time can be up to 8 hours. In certain embodiments, absolute humidity can be about 2.3 grams per cubic meter of air at 25° C. and the period of storage time can be up to 8 hours.

Storage can also include a longer period in which dried compositions are sealed substantially preventing contact with ambient air outside the seal. This period of storage can be for a long time, for example, at least a week, at least a month, at least six months, at least a year or at least two years. A period from one month to two years is exemplary.

Storage temperatures for long-term storage or for long or short-term stability studies include, for example, 0-2° C., 0-4° C., 2-4° C., 2-6° C., 20° C., 25° C., 30° C., 40° C., 50° C., 60° C., as well as subzero temperatures such as −4 to −2° C., −6 to −2° C., −8 to −2° C., −10 to −2° C., −20° C., −40° C., −60° C., −80° C., under liquid nitrogen. Preferably, storage is above freezing point and in the range of about 4-8° C. Accelerated degradation studies can be conducted at about 25° C., about 30° C., about 35° C., about 40° C., for a period of, for example, one hour, two hours, four hours, 24 hours, two days, four days, eight days, one month, and so on. Conditions for storage or, alternatively, for stability can testing, can be those that fluctuate in temperature, such as those that fluctuate from above to below a freezing point.

The absence of inorganic salts reduces loss of enzyme activity and formation of byproducts during storage of bulk reagents before drying, during short term storage of dried composition before sealing, and long term storage after sealing. Preferably enzyme activity after all storage is at least 99% the value before immediately prior to initiating storage, at least 98%, at least 95%, at least 90%, at least 80%, at least 75%, at least 70%, at least 60%, at least 50%, at least 40%, at least 30%, at least 20%, and ranges borded by these percentages, of the value prior to initiating storage, or alternatively, to the value of a comparator sample stored under optimal conditions.

V. Reconstitution

A preferred reconstitution solution provides 3.8-4.4 mM $MgCl_2$, and 50-80 mM KCl in water. The reconstitution solution can also contain 0.012-0.020% methyl paraben, 0.006-0.010% propyl paraben, and/or 0.26% absolute ethanol among other components.

Reconstitution time can be, under 1 sec, under 2 sec, under 5 sec, under 10 sec, under 15 sec, under 20 sec, under 50 sec, or under 60 sec (1 minute), after the addition of an aqueous solution suitable for intended use of the dried composition is contacted with the dried composition, with contact optionally facilitated by any of shaking, tapping vortexing, rocking, drawing in and out of a pipet tip, or folding or squeezing of a malleable vial. An exemplary reconstitution time is 2-10 sec. Reconstitution time can be measured with the reconstitution solution at any of refrigerator temperature (about 4° C.), ambient temperature solution (about 23° C.), or with a warm solution (about 37° C.). Typically, the dried composition has been removed from a refrigerator and is cold before addition of the reconstitution solution. The environment (the room) for any of these procedures is typically ambient temperature of about 23° C. The time at which a substance is determined to be reconstituted can be, for example, the time at which the substance is determined to be completely solubilized. Complete solubilization can be determined by visual inspection, for example, where absence of turbidity or absence of a schlieren pattern is a measure of complete solubilization. Alternatively, complete solubilization can be determined by way of an optical instrument, such as a machine that measures light scattering.

VI. Stability of Compositions

Stability of compositions is typically assessed after reconstitution of a dried product from activity (i.e., rate or yield of amplification) or formation of byproducts. Lack of stability can result from loss of activity or formation of byproducts during storage either before or after drying.

Activity or formation of byproducts can be absolute or relative measures. If relative, the base line for comparison can be a bulk reagent mixture before drying and reconstitution or a control reconstituted mixture differing from that under test in a defined way (e.g., presence of magnesium or other salt or ion thereof). Activity can be assessed by rate of real time amplification or final yield of amplication product or hit rate. Side products can be assayed by one or more of gel electrophoresis, a gel scanner, agarose gels, capillary electrophoresis, and so on.

The activity of a reconstituted amplification mixture (corrected if necessary for any differences due to a different volume of reconstitution relative to the volume of the pre-dried reagent) is preferably within 75, 80, 85, 90, or 95% or is indistinguishable within experimental error from that of the reagent before drying. The side products present within a reconstituted amplification mixture (corrected if necessary for any differences due to a different volume of reconstitution relative to the volume of the pre-dried reagent) are preferably less than 20, 15, 10, 5, 4, 3, 2 or 1% by weight or average moles of the original compounds present in the bulk reagent before drying. Preferably side products are below a limit of detection.

VII. Kits

The dried compositions described above can be provided in a kit. Such a kit can contain the dried compositions in a vessel, such as a tube. In some embodiments, the kit contains a multi-well plate comprising one or more wells. Some kits contain a plurality of dried compositions supplied in separate vessels. Some kits include one or more multi-well plates including multiple dried compositions in one or more sealed well members of the multi-well plates.

Some kits also include a reconstitution solution in a separate vessel from dried compositions. The reconstitution solution can be provided in bulk for dispensing aliquots into individual dried composition vessels or can be provided in the form of one or more unit dosages, each for combination with a single vessel containing a dried composition.

Optionally a vessel containing dried composition and a vessel containing reconstitution solution can be separated by a frangible material. The frangible material can be aluminum foil, polypropylene, polyester, polyvinylchloride (PVC), polyethylene or other similar material. The barrier can include one, two, three or more layers, each layer having the same composition, or each layer having a different composition, such as a foil layer in contact with a PVC layer. Films can be acquired from, e.g., Dow Chemical Co., Midland, MI or Arkema, Inc., King of Prussia, PA. Piercing of the frangible material allows the reconstitution solution to contact the lyophilized composition The kit can be designed to fit into a thermocycler or into an incubator so that enzymatic reactions take place directly in a compartment of the kit to avoid need to transfer compositions to different reaction vessel or containers holding such vessels.

Kits can be adapted for introduction of a user-supplied reagent into a vessel within the kit, for example, by way of a port, a hose, a syringe puncturing a septum (see, US2014/0121515 and US2014/0276356), or alternatively, the user-supplier reagents, such as a nucleic acid template, can be mixed with reagents of the disclosure in a user-supplied container. One or more of the compartments of the kit can be supplied in an empty state and used as a mixing chamber.

EXAMPLES

Example 1. Bulk Reagents

Examples 1 to 3 illustrate making a bulk reagent, drying a single unit dose volume of the bulk reagent to get a SUD dried pellet in a vessel, and reconstituting the dried pellet to get an SUD amplification and detection mixture. Table 1 and Table 2 disclose components of exemplary bulk reagents for drying. The two tables also disclose exemplary single unit dose concentrations. Master mix 1 was a 2× master mix comprising 0.4 mM of each of dATP, dGTP, dCTP and dTTP; 0.8 mM dUTP; BSA, and substantially no inorganic salts. Taq polymerase in Table 1 was in a glycerol free TRIS buffer containing a cationic detergent.

2× Master Mix 2 is: 0.4 mM dATP, dGTP, dCTP, 0.8 mM dUTP, 0.74 Units/µL GoTaq® MDx Hot Start polymerase, glycerol free in proprietary buffer containing Tris and non-acetylated BSA, 0.48 M trehalose.

50× GoScript RT Mix is as follows: 20 U/µL GoScript®, 8 Units/µL RNasin® Plus RNase Inhibitor in Table 2; 10 U/µL GoScript®, 8 Units/L RNasin® Plus in Table 1.

GoScript® RT Custom is a concentrated solution of GoScript RT at 160 U/µL, glycerol free, no RNase inhibitor.

Stabilizers that can be included deamidation inhibitors, anti-oxidants, detergents, and surfactants, such as the surfactants: fatty acid esters of sorbitan polyethoxylates (e.g., polysorbate 20 or polysorbate 80), and poloxamer 188.

TABLE 1

Exemplary Bulk Reagent for Drying

| Description | Bulk Reagent (concentration with appropriate units) | Quantity per Liter | SUD (concentration with appropriate units) | Workable range (concentration with appropriate units) |
|---|---|---|---|---|
| 1.4M Trehalose | 0.30 M | 214 mL | 0.24 M | 0.16-0.32 M |
| Soln, EDTA 0.5M pH 8.0 | 2.19 mM | 4.4 mL | 1.75 mM | 0.0-3.5 mM |
| 2X Master Mix 1, w/o salt, w/o MgCl$_2$ | 1.25 X | 625 mL | 1 X | |
| Taq polymerase (50 U/ul) | 0.4 U/µL | 400 kU (8.00 mL) | 0.32 U/µL | 0.1-1.0 U/ul |
| 50X GoScript ™ RT Mix for 1-Step RT-qPCR, Low Glycerol, Custom | 1.25 X | 25.0 mL | 1 X | |
| GoScript ™ RT Custom Formulation, 160 U/µL | 0.25 U/µL | 250 kU (1.6 mL) | 0.20 U/µL | 0.1-0.6 U/ul |
| 10X oligonucleotide mix | 1.25 X | 125 mL | 1 X | 0.7X-1.3X |

TABLE 2

Exemplary Bulk Reagent for Drying

| Description | Bulk Reagent (concentration with appropriate units) | Quantity per Liter | SUD (concentration with appropriate units) | Workable range (concentration with appropriate units) |
|---|---|---|---|---|
| Solution EDTA 0.5M pH 8.0 | 2.19 mM | 4.38 mL | 1.75 mM | 0.0-3.5 mM |
| 2X Master Mix 2, w/o salt, w/o MgCl$_2$, w/extra Taq Pol, w/ trehalose, w/nucleotides | 1.25 X | 625 mL | 1 X | |
| from trehalose' | 0.30 M | " | 0.24 M | 0.16-0.32 M |
| From Taq Pol | 0.46 U/μL | " | 0.37 U/μL | 0.1-1.0 U/ul |
| 50X GoScript ™ RT Mix for 1- Step RT-qPCR, Low Glycerol, Custom, w/RNasin Plus | 1.25 X | 25.0 mL | 1 X | |
| From RT | 0.5 U/μL | " | 0.4 U/μL | 0.1-0.6 U/ul |
| 10X oligonucleotide mix | 1.25 X | 125 mL | 1 X | 0.7X-1.3X |

TABLE 3

Exemplary Bulk Reagent for Drying

| Description | Stock Concentration | End Concentration | Final Vol |
|---|---|---|---|
| AllStart 2X Master Mix (without KCL and withoutMgCl$_2$) | 2 X | 1 X | 12 ul/reaction |
| 10X PnP Mix | 10 X | 1 X | 2.5 ul/reaction |
| Z05 DNA Polymerase | 200 U/ul | 4 U/ul | 1 ul/50 ul reaction mix volume |
| AMV Reverse Transcriptase | 80 U/ul | 5 U/ul | 3.13 ul/50 ul reaction mix volume |
| T4G32P (protein for unfolding nucleic acids) | 10 U/ul | 2.5 U/ul | 12.50 ul/50 ul reaction mix volume |
| Enzyme Dilution Buffer | | | 33.4 ul/50 ul reaction mix volume |
| 10X oligonucleotide mix | 10 X | 1.25 X | 1 X |

The 10× oligonucleotide mix in each of the bulk amplification reagents for Tables 1 to 3 included collections of primers and probes for performing amplification and detection reactions in the below examples. Ordinarily skilled artisans will understand how to prepare primer and probe mixtures for an amplification reaction (see e.g., Innis, Michael A. et al., *PCR Protocols: A Guide to Methods and Applications*, Academic Press (1990)). For the below examples, primers and probes were present in the bulk reagent at bulk concentrations from about 8 uM to about 12 uM.

Example 2. Lyophilization

In this example, the bulk reaction mixtures are dried using a lyophilizer. 24 microliters of bulk amplification reagents described generally in example 1 is added to a vessel and then loaded into a lyophilization chamber. For the examples herein, 24 μl represents the amount of bulk reagent used to perform an amplification and detection reaction on a single sample (also referred to as a single unit dose or an SUD). In this example, a multiwell plate (specifically a 12-well plate) was used for both the lyophilization reaction and for storage of the lyophilized pellet present in the wells of the multiwell plate. Each of the 12 wells of the 12-well plate received a 24 μl aliquot of the bulk reaction mixture. The reagent in each of the wells represented a single unit dose for performing an amplification and detection reaction on a target nucleic acid. A lyophilization cycle is turned on (about 36 hour run). Following the lyophilization cycle, the 12-well plate is retrieved and transferred to a location where the individual vessels of the 12-well plate are sealed. Vessels are sealed with a metallic foil over the vessel opening. The metallic foil is a low moisture-vapor transmission rate foil. The sealed 12-well plates are then pouched with a desiccant. For use in amplification reactions, the 12-well plates are directly loaded on an instrument. The dried composition within each vessel is manually reconstituted or, in the case of an instrument that is equipped with a reconstitution solution and programed to automate reconstitution of the dried composition, the dried composition is reconstituted by the instrument. A sample is combined with the reagent and an amplification and detection reaction is performed.

Example 3. Reconstitution Solution

This example described one reconstitution solution. The purpose of the reconstitution solution is to rehydrate the dried pellet in preparation for using the reconstituted pellet to perform an amplification and detection reaction on a sample. To each of the 12-wells of the 12-well plate from example 2, 24 μl of reconstitution buffer was dispensed by pre-piercing the foil cover on the well and then dispensing the buffer into the well. Table 4 discloses the reconstitution solution used in these examples, providing both bulk reconstitution solution concentrations and final assay concentrations. Following reconstitution of the dried, target nucleic acids from a sample were added to the wells and a PCR amplification and detection reaction was performed.

TABLE 4

Universal Reconstitution Solution

| Description | Formula weight | Bulk Recon (concentration with appropriate units) | Quantity per Liter | Final Assay Solution (concentration with appropriate units) |
|---|---|---|---|---|
| $MgCl_2$ | 1.00M liq Stk | 5.19 mM | 5.19 mls | 4.15 mM |
| KCl | 74.55 g | 81.3 mM | 6.06 | 65 mM |
| Methyl Paraben | 152.15 g/mol | 0.02% w/v | 0.20 g | .016% |
| Propyl Paraben | 180.2 g/mol | 0.01% w/v | 0.10 g | .008% |
| Ethyl Alcohol, Absolute | 46.07 g/mol | 0.33% v/v | 3.30 mL | 0.26% |

Example 4. Negative Influence of Inorganic Salts on Bulk Reagent

This example describes the negative influence of inorganic salts on bulk reagents. Two bulk reagent mixtures were prepared generally according to example 1 and Table 5. The difference between Bulk Reagent A and Bulk Reagent B in Table 5 was the presence or absence of $MgCl_2$ in the reaction mixtures.

TABLE 5

Bulk Reagents with and without inorganic salts

| | Bulk Reagent A (without $MgCl_2$ and without KCl) | Bulk Reagent B (with $MgCl_2$ and without KCl) |
|---|---|---|
| Trehalose | 0.30 M | 0.30 M |
| Hot Start Taq DNA Polymerase (glycerol free) | 0.46 Units per microliter | 0.46 Units per microliter |
| Reverse Transcriptase | 0.5 Units per microliter | 0.5 Units per microliter |
| RNasin | 0.2 Units per microliter | 0.2 Units per microliter |
| dNTP mix | 0.25 mM dNTP, 0.5 mM UTP | 0.25 mM dNTP, 0.5 mM UTP |
| Nucleic Acids[§] | 7 micromolar (uM) | 7 micromolar (uM) |
| KCl | 0 mM | 0 mM |
| $MgCl_2$ | 0 mM | 2.5 mM |
| Low Glycerol Buffer | 2.7 mM $Na^+$ 0.035 mM $K^+$ | 2.7 mM $Na^+$ 0.035 mM $K^+$ |

[§] Nucleic Acids were a multiplex primer and probe mix made up of the following primer probe sets: for amplification and detection of influenza A there were 2 forward primers, 3 reverse primers, and 3 probes (two different flu A target regions); for influenza B there were 1 forward primer, 1 reverse primer, and 1 probe; for RSV there were 1 forward primer, 1 reverse primer, and 1 probe for RSVA and there were 1 forward primer, 1 reverse primer, and 1 probe for RSVB; and for the internal control there were 1 forward primer, 1 reverse primer, and 1 probe. The value of 7 micromolar is the sum of all primer concentrations wherein each primer is about 400 nM.

Each of liquid bulk reagents A and B were prepared on ice. Bulk reagents A and B were then each separately aliquoted into the wells of a number of multiwell plates (specifically here, 12-well plates were used). These 12-well plates containing either 12 aliquots of bulk reagent A or 12 aliquots of bulk reagent B were then separated into four different incubation conditions: (1) 90 minute incubation on ice; (2) 90 minute incubation at room temperature; (3) 180 minute incubation on ice; or (4) 180 minute incubation at room temperature. Thus, one portion of each bulk reagent mixture was incubated at room temperature for 180 minutes and the other portion was incubated on ice for 180 minutes. Likewise, one portion of each bulk reagent mixture was incubated at room temperature for 90 minutes and the other portion was incubated on ice for 90 minutes. In all cases, addition of the nucleic acid component to the reaction mixture (added as the final component) indicated the start of the incubation time.

Following the incubation times, the aliquoted amplification reactions in the 12-well plates were then lyophilized until substantially dry compositions were obtained. Each of the resulting dried compositions in a well of the 12-well plates represented a dried single unit dose for a triplex amplification and detection reaction to identify one or more of influenza A, influenza B and respiratory syncytial virus B in a sample.

The dried compositions were reconstituted with a buffer containing 65 mM of KCl, methyl and propyl paraben at 0.02% w/v and 0.01% w/v, respectively, and 0.33% v/v ethyl alcohol absolute. The reconstitution solution for dried compositions made from bulk reagent A also contained 2.5 mM $MgCl_2$.

All three of influenza A, influenza B, and respiratory syncytial virus B positive samples were combined into the reconstituted reaction mixtures at 3 times their LoD, such that all components of the reconstituted mix were at about 80% of their bulk reagent concentration. These positive samples are extracted viruses in a negative plasma combined with a transport medium and serially diluted to the desired concentration (with the exception that the RSVB sample serial dilution was off by a factor of 10). As indicated for Table 6, the primers and probe mix was designed to specifically detect each of the three viral targets, namely influenza A, influenza B, or respiratory syncytial virus type B, in a separate fluorescent channel, albeit in a single molecular reaction.

The samples were assayed using a real-time PCR compatible thermal cycler (ABI 7500FAST, Applied Biosystems, Carlsbad, CA). Results are as follows (Table 6, FIGS. 3A-C). The percent positive value in the table represents the number of samples that had RFU values that exceeded the threshold value as a percentage of the 12 samples tested. In designing and assembling the assays, what is preferred is that the amount of virus (viral particles per assay) is an amount sufficient to give at least a 950% positive for the particular assay designated as a positive control.

this example). The single unit dose pellets were made by drying a bulk reagent generally as described above. Immediately after synthesis, bulk reagent A and bulk reagent B were each aliquoted into separate multiwell reaction plates (12-well) and dried using a lyophilizer. Following lyophilization, the multiwell plates containing dried pellets were placed in a nitrogen gas environment having a relative humidity of about 5%, and the multiwell plates were sealed by covering the well openings with a foil. Sealed plates were placed into an aluminum pouch containing a desiccant, and the pouches were then sealed. The sealed pouches containing the dried pellets in multiwell plates were stored for eight days at 4° C.

TABLE 6

Results

| Condition | Influenza A Avg RLU For Positive Samples No. Positive/% Positive | Influenza B Avg RLU For Positive Samples No. Positive/% Positive | RSVB Avg RLU For Positive Samples No. Positive/% Positive |
|---|---|---|---|
| #1 Bulk Reagent B 90 min Incubation On Ice | 602,587 6 of 12/50% | 303,112 11 of 12/92% | 320,017 12 of 12/100% |
| #2 Bulk Reagent A 90 min Incubation On Ice | 1,235,701 12 of 12/100% | 1,028,348 12 of 12/100% | 1,107,497 12 of 12/100% |
| #3 Bulk Reagent B 90 min Incubation Room Temp | 163,536 4 of 12/33% | 94,229 11 of 12/92% | 684,384 12 of 12/100% |
| #4 Bulk Reagent A 90 min Incubation Room Temp | 1,699,434 12 of 12/100% | 1,832,464 12 of 12/100% | 1,064,536 12 of 12/100% |
| #5 Bulk Reagent B 180 min Incubation On Ice | 576,226 12 of 12/100% | 530,568 12 of 12/100% | 1,048,669 12 of 12/100% |
| #6 Bulk Reagent A 180 min Incubation On Ice | 1,396,077 12 of 12/100% | 1,314,236 12 of 12/100% | 934,325 12 of 12/100% |
| #7 Bulk Reagent B 180 min Incubation Room Temp | 34,092 (below RLU threshold) 0 of 12/0% | 57,484 3 of 12/25% | 394,945 12 of 12/100% |
| #8 Bulk Reagent A 180 min Incubation Room Temp | 1,970,034 12 of 12/100% | 1,896,883 12 of 12/100% | 1,074,004 12 of 12/100% |

These results indicate that bulk reagent (prelyophilization solutions without MgCl$_2$ and KCl) are stable to at least 180 minutes at room temperature. Dried SUD pellets from bulk reagent A, once reconstituted and combined with samples, provide amplification and detection reactions that are more robust than those provided by dried SUD pellets from bulk reagent B. Bulk reagent B, when incubated at room temperature or even on ice for as few as 90 minutes, then dried and reconstituted to generate an amplification reaction mixture, provided in an amplification reaction a relatively lower signal and an abundance of small side products than did bulk reagent A under the same conditions. Bulk reagents containing little to no inorganic salts are useful for drying to generate a dried composition containing components for an amplification reaction, including polymerase enzyme components, dNTPs and nucleic acids.

Example 5. Stability of Dried Pellets, with or without Salts

This example compares the stability of single unit dose dried pellets containing salts with single unit dose dried pellets containing no salts (less than 5 mM inorganic salt in Following the eighth day, the pouched multiwell plates were transferred into one of three conditions as follows: Condition #1-1 subset of pouched multiwell plates containing dried pellets from bulk reagent A and 1 subset of pouched multiwell plates containing dried pellets from bulk reagent B were removed from the pouch and placed in a 15° C. environment with 70% relative humidity; Condition #2-1 subset of pouched multiwell plates containing dried pellets from bulk reagent A and 1 subset of pouched multiwell plates containing dried pellets from bulk reagent B were removed from the pouch an placed in a 45° C. environment with 15% relative humidity (accelerated stability); and Condition #3-1 subset of pouched multiwell plates containing dried pellets from bulk reagent A and 1 subset of pouched multiwell plates containing dried pellets from bulk reagent B were placed at 4° C. (the multiwell plate was in a pouch with desiccant, thus humidity was zero percent). Plates were left at these conditions for thirty additional days.

Figure 1:
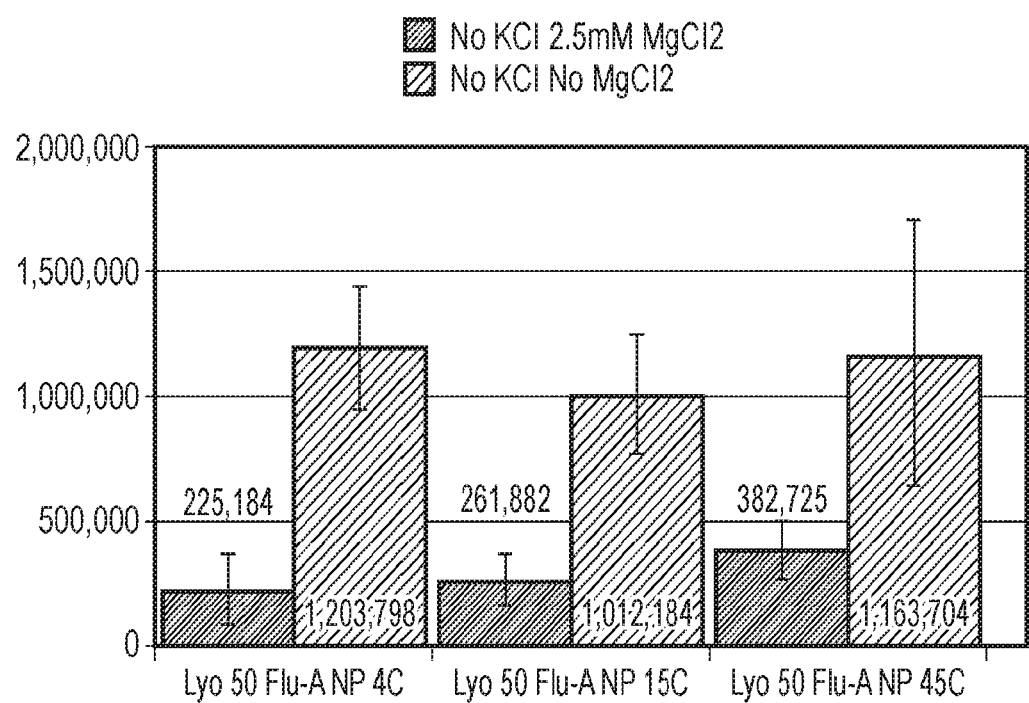
FIG. 1 shows activity determined in samples that had been lyophilized with or without magnesium, and then stored dry at various temperatures.

At the conclusion of the incubation, the dried pellets from each of the conditions were reconstituted in a buffer containing 100 mM KCl and sufficient MgCl$_2$ for a final concentration of 2.5 mM and tested for amplification and detection of an influenza A target using a real-time PCR thermal cycler (ABI PRISM 7000, Applied Biosystems, Carlsbad, CA). Briefly, the influenza A targets were extracted in a negative pool at LOD 10^0 (+/−1 log) along with a comparable liquid control. Results are shown in Table 7 and in FIG. 1.

TABLE 7

|  | Average Total RFU (N = 4) |
|---|---|
| Bulk Reagent A 4 .deg. C./4 .deg. C. | 1,203,798 |
| Bulk Reagent B 4 .deg. C./4 .deg. C. | 255,184 |
| Bulk Reagent A 4 .deg. C./15 .deg. C. | 1,012,184 |
| Bulk Reagent B 4 .deg. C./15 .deg. C. | 261,882 |
| Bulk Reagent A 4 .deg. C./45 .deg. C. | 1,163,704 |
| Bulk Reagent B 4 .deg. C./45 .deg. C. | 382,725 |

These results show that single amplification reaction dried pellets containing less than 5 mM inorganic salts have higher RFU values following storage in a number of different temperature and humidity conditions compared to single amplification reaction dried pellets containing more than 5 mM inorganic salt.

Example 6. Influence of Holding Time Prior to Filling Cartridges with Reagent

Table 8 discloses results from a stability study, where all lyophilized samples were prepared from the same bulk reagent. This example describes the stability of a dried pellet prepared generally as shown above. A bulk reagent containing polymerase enzymes, dNTPs and nucleic acids was prepared without $MgCl_2$ and without KCl. The bulk reagent was divided into four separate portions of equivalent compositions, and each of the four portions were either: (1) incubated at room temperature for 45 minutes then dried; (2) incubated at room temperature for 4 hours then dried, (3) incubated at room temperature for 8 hours and then dried; or (4) immediately dried without incubation.

The resulting dried compositions were then transferred to an aluminum pouch containing a 1.5 g desiccant pillow and the pouch was then sealed. The sealed pouches were stored under conditions to simulate an accelerated stability equivalent of 22.5 months at 5° C. Following the accelerated stability incubation the dried compositions were reconstituted and the resultant amplification reactions were used in an assay for amplification and detection of influenza A samples ($TCID_{50}$/mL=1). The results in Table 8 demonstrate that there is no disruption of amplification and detection assay performance when a bulk solution containing no $MgCl_2$ and no KCl is incubated for up to 8 hours at room temperature prior to drying. Reconstituted dried compositions provide amplification and detection reactions that are robust and provide reproducible results, even when tested on samples containing low viral titer.

TABLE 8

| Condition (n = 12) | Total Cycle Time (Avg Ct/±SD Ct) |
|---|---|
| Room Temperature for 45 minutes | 34.5/±0.58 |
| Room Temperature for 4 hours | 34.4/±0.32 |
| Room Temperature for 8 hours | 33.9/±0.60 |
| No Incubation | 34.3/±0.39 |

This study reveals that varying the bulk hold time for liquid lyo reagent during filling of the vessels does not reduce enzymatic activity (FIG. 2). To test stability of the bulk reagent during the filling of the vessels, a study exposing the bulk mix to ambient temperature for up to 8 hours prior to lyophilization was performed. Individual Flu A/B/RSV bulk liquid lyo reagent mixes were prepared and incubated for 45 minutes, 4 hours, and 8 hours, at room temperature and then used to generate lyo pellets. These pellets were then pouched and exposed to 45° C. for 22 days to simulate an accelerated stability equivalent to a shelf life of 22.5 months at 5° C., prior to testing with a low level viral titer. The results (FIG. 2) show that there is no disruption of assay performance when the liquid lyo bulk is stored at ambient conditions for up to 8 hours.

The respective RFU for the histogram bars are, 824,895; 806,570; 855,772; and 1,162,967. The values for Ct (emergence time) were as follows. For the liquid control (Avg Ct=34.3), for 45 minutes (Avg Ct=34.5), for 4 hours (Avg Ct=34.4), and for 8 hours (Avg Ct=33.9). The respective standard deviations for the Ct values were, 0.39, 0.58, 0.32, and 0.60 (FIG. 2).

Example 7. Reconstitution Time Course Study

This concerns the experiment shown in Table 9. The experimental set-up to determine if incubating a dried pellet comprising no KCl and 2.5 mM $MgCl_2$ in reconstitution solution impact assay activity. To summarize, dried pellet SUDs without KCl but with 2.5 mM $MgCl_2$) were prepared by lyophilization of a bulk reagent, as generally described above. Following lyophilization, the dried pellet SUDs were sealed under nitrogen at 5% relative humidity, pouched with a desiccant, and then stored at 4° C. for 27 days. After the 27 day incubation, the dried pellets were reconstituted and used to detect Flu-A from samples, where all assays had 100 mM KCl and 2.0 mM $MgCl_2$, as final concentrations in the reaction mixture.

No KCl/2.5 mM $MgCl_2$ SUDs were reconstituted with 125 mM KCl and were allowed to incubate for 0, 5, 10 or 15 minutes on ice prior to transfer to a pre-chilled PCR plate and the addition of target. The plate was sealed and samples were spun for 1 minute. The plate was then transferred to the pre-warmed ABI 7500 FAST instrument (Applied Biosystems, Carlsbad, CA). Assays were run on the ABI under the 54-minute thermal profile with N=4 replicates and threshold set to 25,000. Table 9 discloses the results.

TABLE 9

Reagent performance time course after reconstitution

| Condition | Average RFU | StDev |
|---|---|---|
| No KCl SUD, incubated zero minutes | 2,356,231 | 492,540 |
| No KCl SUD incubated 5 minutes | 1,806,528 | 418,064 |
| No KCl SUD incubated 10 minutes | 1,532,903 | 425,275 |
| No KCl SUD incubated 15 minutes | 1,668,826 | 1,116,796 |
| Liquid control | 4,075,739 | 154,846 |

Example 8. Impact of Magnesium Chloride on Stabilisation

This example investigated the impact of the removal of $MgCl_2$ from a bulk reagent master mix, including buffer, trehalose, EDTA, nucleotide triphosphates, primers, probes and enzymes, on stabilisation. The removal of $MgCl_2$ from the bulk reagent was found to stabilize the formulation from 90 minutes for up to 7.75 hours at room temperature prior to lyophilization, as measured by activity post reconstitution with water and $MgCl_2$. Addition of EDTA to the lyophilised pellet is useful for chelating excess $MgCl_2$ in a reconstitution buffer.

Primers, probes, and triphosphates can be provided in a buffered master mix, with enzymes spiked in prior to the amplification reaction. For some amplification reactions, it can be desirable to have the enzyme in the final master mix and lyophilize it in a "ready to use" form with a universal reconstitution solution of water and $MgCl_2$. This avoids the need to spike the mix prior to the amplification reaction. Magnesium serves as a complexing agent (catalyst) for the polymerization reaction. With no target present, non-specific amplification can occur which can deplete the reaction mix of the necessary triphosphates. Keeping the materials at 2-8° C. and loading into a prechilled lyophilizer can be used to slow the reaction kinetics which can slow down the depletion of the triphosphates from the reaction mix. However, even at 2-8° C. stability of the reaction mix may be only 90 minutes. Moreover, adherence to these limitations during routine manufacturing requires the use of cooling systems to maintain the bulk solution temperature at the desired temperature, as well as pre-chilling steps and the like.

Removal of $MgCl_2$ from the bulk reagent including buffer, trehalose, triphosphates, EDTA, primers, probes and enzymes and placement into a reconstitution solution containing water and $MgCl_2$ was considered as a way to prevent or minimise non-specific amplification even though it serves as a catalyst for the polymerization reaction. The addition of EDTA solution to the master mix containing buffer, trehalose, triphosphates, primers, probes and enzymes could be used to chelate excess magnesium in the universal recon for each analyte. Paired amplification reactions with and without $MgCl_2$ were performed and ran under wet chemistry conditions to assess the impact on stability. The results are shown in FIG. 4. Studies without magnesium in the bulk reagent containing buffer, trehalose, triphosphates, EDTA, primers, probes and enzymes showed room temperature stability for 180 minutes (see lanes 6 and 8, which show the same bands on the bioanalyzer gel compared to non-specific smears in lanes 5 and 7 with $MgCl_2$ present). Follow up studies are shown in FIG. 2. Here, nucleic acid amplification of a target was carried out under three different conditions: (1) Fresh Liquid Control including buffer, trehalose, triphosphates, EDTA, primers, probes, $MgCl_2$ and enzymes, with enzyme spiked immediately before initiating the PCR reaction; (2) Lyo 67 RT for 3.75 hours including buffer, trehalose, triphosphates, EDTA, primers, probes and enzymes. The solution was held for 3.75 hours, then lyophilized. Post lyophilization, the pellet was reconstituted in water and $MgCl_2$ immediately prior to initiation of the PCR reaction; and (3) Lyo 67 RT for 7.75 hours including buffer, trehalose, triphosphates, EDTA, primers, probes and enzymes. The solution was held for 7.75 hours, then lyophilized. Post lyophilization, the pellet was reconstituted in water and $MgCl_2$ immediately prior to initiation of the PCR reaction. This experiment established stability of the bulk reagent containing buffer, trehalose, triphosphates, EDTA, primers, probes and enzymes for 7.75 hours at room temperature prior to lyophilization without non-specific amplification.

Removal of $MgCl_2$ from the bulk reagent provides a room temperature stable master mix containing buffer, trehalose, triphosphates, EDTA, primers, probes and enzymes.

Example 9. Effect of Potassium Chloride (KCl) on Sublimation During Lyophilization This example investigated the effect of potassium chloride (KCl) on sublimation during lyophilization. PCR requires KCl for PCR amplification. The results of this study indicated that low concentrations of KCl (<10 mM, 0.391 µg/µL Potassium) do not significantly affect lyophilization. Conversely, KCl concentrations as high a 126 mM (4.92 µg/µL Potassium) inhibit the removal of water from the pellet during lyophilization. Residual water is considered an "impurity" that adversely affects stability. Excluding or minimizing the amount of KCl in the lyophilised bulk reagent is desirable in certain embodiments.

The efficiency of lyophilization in the presence of three concentrations of KCl was investigated by measuring the post-lyophilization residual moisture content therein. Higher levels of residual moisture are known to inhibit the sublimation process.

Fourier Transform near-infrared (FT-nIR) spectroscopy was used to measure the relative moisture content in the lyophilised bulk reagent. Water-OH bonds are known to absorb energy at the nIR spatial wave length of 5170 cm$^{-1}$ ($A^{5170}$).

Three aqueous bulk reagent formulations were prepared. The composition of each is shown in Table 10.

TABLE 10

Composition of aqueous bulk reagent formulations

| | Formulation | | |
|---|---|---|---|
| Component | 1 | 2 | 3 |
| Tris Buffer | 27 mM | 29 mM | 30 mM |
| pH | 8.0 | 8.0 | 8.0 |
| Trehalose | 0.46 M | 0.46 M | 0.46 M |
| KCl | 0 | 126 mM | 6.3 mM |
| DTT | 1.3 mM | 1.3 mM | 1.3 mM |
| Tween | 0.7% | 0.7% | 0.7% |

1.25X Probe/Primer Mix (Relative to final assay concentration)
1.25X Taq Polymerase (Relative to final assay concentration)
1.25X Reverse Transcriptase (Relative to final assay concentration)

1.45 mL of each formulation was filled into two 10 mL glass vials for each KCl concentration. The vials were partially stoppered with butyl stoppers. All vials were lyophilized together. At the conclusion of lyophilization, the vials were sealed under anhydrous nitrogen gas. All of the sealed vials were removed from the lyophilizer and crimp seals were applied. The vials were then measured for residual moisture content by FT-nIR spectroscopy. To account for moisture level lag time drift, measurements were obtained over 10 days. The time points were as follows: day 0, day, 1, day 3, day 7 and day 10. The residual moisture content was measured by FT-nIR spectroscopy yielding a nIR absorbance parameter at 5170 cm$^{-1}$. For each formulation the absorbance parameters were averaged, then normalized to the average parameter obtained from the reference sample, Formulation 1 (0 µg/µL KCl). The following calculation was used.

$$\text{Normalized Sample Parameter} = \frac{\text{Sample Abs (Time } t\text{)}}{\text{Formulation 1 abs (Time } t\text{)}}$$

Tables 11 and 12 show the FT-nIR absorbance results.

TABLE 11

FT-nIR Absorbance Results*

| | Day 0 | | | Day 1 | | | Day 3 | | |
|---|---|---|---|---|---|---|---|---|---|
| Vial ID | $A_{5170}$ | Ave $A_{5170}$ | Normalized | $A_{5170}$ | Ave $A_{5170}$ | Normalized | $A_{5170}$ | Ave $A_{5170}$ | Normalized |
| 1-1 | 0.0481 | 0.0506 | 1.00 | 0.0557 | 0.0559 | 1.00 | 0.0610 | 0.0610 | 1.00 |
| 1-2 | 0.0531 | | | 0.0560 | | | 0.0610 | | |
| 2E-1 | 0.1094 | 0.1083 | 2.14 | 0.1214 | 0.1182 | 2.12 | 0.1250 | 0.1248 | 2.05 |
| 2E-2 | 0.1072 | | | 0.1150 | | | 0.1245 | | |
| 2F-1 | 0.0667 | 0.0548 | 1.08 | 0.0711 | 0.0612 | 1.09 | 0.0749 | 0.0656 | 1.07 |
| 2F-2 | 0.0429 | | | 0.0512 | | | 0.0562 | | |

TABLE 12

FT-nIR Absorbance Results Continued From Table 11*

| | Day 7 | | | Day 10 | |
|---|---|---|---|---|---|
| $A_{5170}$ | Ave $A_{5170}$ | Normalized | $A_{5170}$ | Ave $A_{5170}$ | Normalized |
| 0.0651 | 0.0653 | 1.00 | 0.0669 | 0.0667 | 1.00 |
| 0.0655 | | | 0.0665 | | |
| 0.1274 | 0.1251 | 1.92 | 0.1271 | 0.1215 | 1.82 |
| 0.1228 | | | 0.1159 | | |
| 0.0756 | 0.0676 | 1.03 | 0.0847 | 0.0729 | 1.09 |
| 0.0595 | | | 0.0611 | | |

FIGS. 6 and 7 show the effect of increasing the concentration of KCl. The graphs show that the presence of 6.3 mM KCl did not significantly increase the normalized absorbance parameter. Thus from these data, low concentrations of KCl did not significantly inhibit removal of water during lyophilization. Conversely, 126 mM KCl (20 fold increase) induced a 2 fold increase in the normalized absorbance parameter, indicating higher residual moisture levels as compared to the reference. Thus higher concentrations of KCl impact moisture removal.

*Vial ID in Table 11 and Table 12 relates to Table 10 conditions like so: Table 10 Formulation 1 is Vial ID 1-1 & 1-2 in Tables 11 & 12; Table 10 Formulation 2 is Vial ID 2E-1 & 2E-2 in Tables 11 & 12; and Table 10 Formulation 3 is Vial ID 2F-1 & 2F-2 in Tables 11 & 12.

Lyophilization of the aqueous bulk reagent tolerates small amounts of KCl (approximately 6.3 mM in this example). KCl in higher concentrations can affect the hygroscopicity of the dried pellet resulting in absorption of water from the environment, and in turn resulting in a lest robust reaction mixture.

Example 10. Determining the Post-Lyophilized Stability of a Lyophilized Bulk Reagent Ambient and controlled glovebox experiments using post-lyophilized aliquots of bulk reagent indicated that a minimized/no salt formulation exposed to 10% relative humidity for less than 8 hours resulted in acceptable assay performance. Salt-in formulations and/or formulations exposed to higher relative humidity post-lyophilization did not result in acceptable assay performance.

The aim of this example was to determine the post-lyophilized stability of a lyophilized bulk reagent sealed in multi-well plates and hermetically sealed to protect from ambient moisture (in pouches) under ambient humidity conditions and under controlled 10% relative humidity conditions. In addition to the specific experiment described here, multiple additional studies using additional time points and formulation variants were completed.

Multiwell plates were filled with aliquots of bulk reagent while the plates were kept at 2°-8° C. on ice. Sufficient quantities of all required components were mixed to generate a bulk reagent having a volume sufficient to fill 30 multiwell plates plus 5% overage. Mixing was done according to the following instructions. Add, in order: nuclease-free water, 2× glycerol-free GoTaq master mix (formulations are shown below), 1.2 M Trehalose, 10× Probe/Primer Mix, and 50× Promega RT (0.5% Glycerol formulation for lyophilization). The wells of a number of multiwell plates were filled with 24 µl bulk reagent per well within 1 hour. Multiwell plates were placed on ice to pre-equilibrate at 2° C.-8° C. prior to the filling of tubes. The liquid bulk reagent was dispensed at the bottom of each tube. During the 1 hour fill window, the multiwell plates were kept on ice. Filled multiwell plates were loaded into the lyophilization chamber within 30 minutes after completion of fill. The filled multiwell plates were then exposed to lyophilization conditions. Following the lyophilization process the multiwell plates, were covered/stoppered prior to being retrieved from the lyophilization chamber. Two multiwell plates were transferred to the lab bench. The remaining multiwell plates were transferred to a 10% relative humidity pre-equilibrated glove box to serve as T=0 samples; they were uncovered/unstopped and then heat-sealed after various durations of time as indicated in Table 13. A sealing time of 6 seconds and a sealing temperature of 169° C. is used. Within 5 minutes, the sealed multiwell plates were transferred into a zip-lock foil pouch containing a desiccant pillow and then heat-sealed. For the other multiwell plates on the lab bench, they were uncovered/unstopped and exposed to the ambient atmosphere for various time periods, as shown in Table 13 below.

The relative humidity and temperature at the time of exposure, sealing, and pouching was recorded. After the exposure, the multiwell plates were heat sealed with foil stock using a sealing time of 6 seconds and a sealing temperature of 169° C. The heat-sealing process was done at the exposure conditions (i.e. the multiwell plates exposed to lab atmosphere were sealed in the lab and multiwell plates exposed to a de-humidified condition were sealed at the de-humidified condition), using the same sealing time/temp parameters as above. Within 5 minutes, the sealed multiwell plates were transferred into a zip-lock foil pouch containing a desiccant pillow and the pouch is heat sealed. All sealed pouches were then stored at 2-8° C.

Two multiwell plates were run per time point. Under ambient conditions, post-lyophilisation, the multiwell plates were sealed for 0, 4 and 8 hours (see Table 13). Under 10% relative humidity conditions, post-lyophilisation, the multiwell plates were sealed for 0, 4, 8 and 24 hours (see Table 13). Two multiwell plates per time point times number of conditions=2*3 (ambient=6), and 2*4 (10% relative humidity glove box=8), respectively.

Formulation without salt were prepared using 2× GoTaq master mix, glycerol free+10× Probe/Primer+Trehalose+50×RT. For example, for 30 multiwell plates, add, in order: 449 µl Nuclease Free Water, 4.81 ml 2× GoTaq Master Mix (B, No Salt) (1.25× final), 1.28 ml 1.2 M Trehalose (0.2 M final), 963 µl 10× Probe/Primer Mix (1.25× final), 193 µl 50×RT (1.25× final)=7.70 mls No-salt mix; dispense 24 µl for 300 tubes, use repeat pipettor.

Formulation with salt were prepared using 2× GoTaq master mix, glycerol free+10× Probe/Primer+Trehalose+50×RT. For example, for 38 multiwell plates, add, in order: 560 µl Nuclease-free Water, 6.00 mls 2× GoTaq Master Mix (B, contains salt) (1.25× final), 1.60 mls 1.2 M Trehalose (0.2 M final), 1.20 mls 10× Probe/Primer Mix (1.25× final), 240 µl 50×RT (1.25× final)=9.60 mls salt-containing mix; dispense 24 µl for 380 tubes; use repeat pipettor.

Multiwell plates were tested for performance according to Table 13. In step A of Table 13, the formulation without salt was filled into the multiwell plates and lyophilized. Post-lyophilisation, the multi-well cartridges were sealed following exposure to the condition and for the durations indicated. In step B of Table 13, the formulation without salt was filled into the multi-well cartridges and lyophilized. Post-lyophilisation, the multi-well cartridges were sealed following exposure to the condition and for the durations indicated. In step C of Table 13, the formulation with salt was filled into the multi-well cartridges and lyophilized. Post-lyophilisation, the multi-well cartridges were sealed following exposure to the condition and for the durations indicated.

TABLE 13

Performance test set-up. Each X represents a minimum of two multiwell plates.

| Step | Salt in Formulation | Ambient Conditions (Hours) | | | 10% RH Glove Box (Hours) | | | |
|---|---|---|---|---|---|---|---|---|
| | | 0 | 4 | 8 | 0 | 4 | 8 | 24 |
| A | N | X | X | X | | | | |
| B | N | | | | X | X | X | X |
| C | Y | | | | X | X | X | X |

Ambient and glovebox temperatures were approximately 25° C. Results of this and related experiments indicated that exposure of the no-salt formulation to 10% relative humidity for less than 8 hours resulted in acceptable assay performance. In this example, a duration of less than 8 hours at 10% relative humidity (2.3 g/m$^3$ at 25° C.) with a minimum/no salt formulation results in acceptable assay performance.

The present disclosure is not to be limited by compositions, reagents, methods, diagnostics, laboratory data, and the like of the present disclosure, and that the present disclosure is not be limited by any preferred embodiments that are disclosed herein. Unless otherwise apparent from the context, any embodiment, step, feature, aspect or the like can be used in combination with any other. All references cited herein are incorporated by reference to the same extent as if each individual patent, and published patent application, as well as figures, drawings, sequence listings, compact discs, and the like, was specifically and individually indicated to be incorporated by reference.

What is claimed is:

1. A composition comprising an aqueous solution containing a reverse transcriptase, another polymerase, a bulking agent consisting essentially of trehalose at a concentration from about 0.16 M to about 0.32 M, a detergent, an organic buffer, from 0.1 mM to 0.3 mM of dATP, from 0.1 mM to 0.3 mM of dGTP, from 0.1 mM to 0.3 mM of dCTP, from 0.2 mM to 0.6 mM of dTTP or dUTP, RNase inhibitor and at least two oligonucleotides useful for performing a molecular assay, wherein the aqueous solution has a concentration of $Mg^{2+}$ of less than 0.1 mM and a concentration of $K^+$ of less than 1 mM.

2. The composition of claim 1, wherein the at least two oligonucleotides are selected from the group consisting of: an amplification oligonucleotide, a detection probe oligonucleotide, a target capture probe oligonucleotide, an adaptor oligonucleotide, and combinations thereof.

3. The composition of claim 1, wherein the aqueous solution comprises an inorganic salt concentration of 1 mM or less.

4. The composition of claim 1, wherein the aqueous solution comprises a mass per microliter of inorganic salt from about 0.075 µg/µl to about 0.058 µg/µl and wherein the aqueous solution comprises a mass per microliter of chloride ions from about 0.071 µg/µl to about 0.018 µg/µl.

5. The composition of claim 3, wherein the inorganic salt concentration of the aqueous solution is less than 1 mM sodium chloride.

6. The composition of claim 1, wherein the other polymerase is present in the aqueous solution at a concentration from about 0.20 U/µl to about 0.72 U/µl in the aqueous solution.

7. The composition of claim 6, wherein the other polymerase is present in the aqueous solution at a concentration selected from: 0.25 U/µl, 0.30 U/µl, 0.32 U/µl, 0.4 U/µl, 0.5 U/µl, 0.45 U/µl, and 0.72 U/µl.

8. The composition of claim 1, wherein the reverse transcriptase is present in the aqueous solution at a concentration from about 0.1 U/µl to about 0.6 U/µl.

9. The composition of claim 1, wherein the RNase inhibitor is at a concentration from about 0.12 U/µl to about 0.20 U/µl.

10. The composition of claim 1, wherein the aqueous solution further comprises a chelating agent.

11. The composition of claim 10, wherein the chelating agent is EDTA and is present in the aqueous solution at a concentration from 1.5 mM to 2.0 mM.

12. The composition of claim 1 containing no magnesium ions.

13. A dried composition made by drying a composition comprising an aqueous solution containing a reverse transcriptase, another polymerase, a bulking agent consisting essentially of trehalose at a concentration from about 0.16 M to about 0.32 M, a detergent, an organic buffer, from 0.1 mM to 0.3 mM of dATP, from 0.1 mM to 0.3 mM of dGTP, from 0.1 mM to 0.3 mM of dCTP, from 0.2 mM to 0.6 mM of dTTP or dUTP, RNase inhibitor and at least two oligonucleotides useful for performing a molecular assay, wherein the aqueous solution has a concentration of $Mg^{2+}$ of less than 0.1 mM and a concentration of $K^+$ of less than 1 mM.

14. A method of forming a mixture for use in performing a nucleic acid based amplification reaction, the method comprising combining a reconstitution solution and the dried composition of claim 13, wherein the reconstitution solution comprises at least one inorganic salt.

15. The method of claim 14, wherein the reconstitution solution comprises $MgCl_2$ at a concentration from about 3.8 mM to about 4.4 mM, KCl at a concentration from about 50 mM to about 80 mM, or both.

16. The method of claim 15, wherein the reconstitution solution comprises, methyl paraben at a concentration from about 0.012% w/v to about 0.020% w/v, propyl paraben at a concentration from about 0.006% w/v to about 0.010% w/v, absolute ethanol at a concentration from about 0.20% v/v to about 0.30% v/v, or a combination thereof.

17. The method of claim 16, wherein the concentration of the methyl paraben in the reconstitution solution is 0.016% w/v, the concentration of the propyl paraben in the reconstitution solution is 0.008% w/v and the concentration of the absolute ethanol is present in the reconstitution solution at about 0.26% v/v.

\* \* \* \* \*

UNITED STATES PATENT AND TRADEMARK OFFICE
CERTIFICATE OF CORRECTION

PATENT NO. : 12,195,792 B2
APPLICATION NO. : 16/074593
DATED : January 14, 2025
INVENTOR(S) : Steven Mauch et al.

It is certified that error appears in the above-identified patent and that said Letters Patent is hereby corrected as shown below:

In the Specification

In Column 9, Line 30, delete "amplication" and insert -- amplification --, therefor.

In Column 15, Line 52, delete "Iuviquat™," and insert -- Luviquat™, --, therefor.

In Column 16, Line 52, delete "WO)" and insert -- WO --, therefor.

In Column 24, Lines 16-17, delete "Drying Lyophilization" and insert -- Drying/Lyophilization --, therefor.

In Column 25, Line 14, delete "(N P" and insert -- (NP --, therefor.

In Column 26, Line 23, delete "borded" and insert -- bordered --, therefor.

In Column 27, Line 7, delete "amplication" and insert -- amplification --, therefor.

In Column 28, Line 6, delete "composition" and insert -- composition. --, therefor.

In Column 33, Line 12, delete "950%" and insert -- 95% --, therefor.

In Column 36, Line 30, delete "MgCl$_2$)" and insert -- MgCl$_2$ --, therefor.

Signed and Sealed this
Thirteenth Day of January, 2026

John A. Squires
*Director of the United States Patent and Trademark Office*